United States Patent
Libsch et al.

(10) Patent No.: US 10,422,672 B1
(45) Date of Patent: Sep. 24, 2019

(54) 2D NANOPARTICLE MOTION SENSING METHODS AND STRUCTURES

(71) Applicant: International Business Machines Corporation, Armonk, NY (US)

(72) Inventors: Frank Libsch, White Plains, NY (US); Venkat K. Belagurusamy, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 8 days.

(21) Appl. No.: 15/915,452

(22) Filed: Mar. 8, 2018

(51) Int. Cl.
   *G01F 1/58* (2006.01)
   *G01F 23/26* (2006.01)
   *G06F 3/147* (2006.01)

(52) U.S. Cl.
   CPC .............. *G01F 1/584* (2013.01); *G06F 3/147* (2013.01)

(58) Field of Classification Search
   CPC .................................. G01F 1/58; G01F 23/26
   See application file for complete search history.

(56) References Cited

U.S. PATENT DOCUMENTS

| | | | |
|---|---|---|---|
| 6,905,586 B2 | 6/2005 | Lee et al. | |
| 7,496,450 B2 | 2/2009 | Ortiz Aleman et al. | |
| 8,246,910 B2 | 8/2012 | Dhirani et al. | |
| 8,614,707 B2 | 12/2013 | Warsito et al. | |
| 8,882,980 B2 | 11/2014 | Ling et al. | |
| 8,966,973 B1* | 3/2015 | Milone | G01F 23/268 73/304 C |
| 9,259,168 B2 | 2/2016 | Marashdeh et al. | |
| 2008/0121045 A1 | 5/2008 | Cole et al. | |
| 2009/0242429 A1 | 10/2009 | Sitdikov et al. | |
| 2011/0079078 A1* | 4/2011 | Ho | G01F 23/268 73/304 C |
| 2013/0085365 A1 | 4/2013 | Marashdeh et al. | |

(Continued)

FOREIGN PATENT DOCUMENTS

| | | |
|---|---|---|
| CN | 103175580 A | 6/2013 |
| WO | 2009053870 A2 | 4/2009 |

OTHER PUBLICATIONS

M. Bardelli et al., "Epitope mapping by solution NMR spectroscopy." Journal of Molecular Recognition, vol. 28, No. 6, 2015, pp. 393-400.

(Continued)

*Primary Examiner* — Jewel V Dowtin
(74) *Attorney, Agent, or Firm* — Patterson + Sheridan, LLP

(57) ABSTRACT

A method, structure and system for capacitive sensing is provided. The structure includes: one or more first conductive lines arranged in a first arrangement in relation to a first substrate, one or more second conductive lines connected arranged in a second arrangement in relation to a second substrate, one or more first vias embedded on the first substrate and connecting one or more first electrodes to each respective one of the one or more first conductive lines; and one or more second vias embedded on the second substrate and connecting the one or more second electrodes to each respective one of the one or more second conductive lines, where the one or more first conductive electrodes and the second one or more electrodes are parallel and overlapping with respect to one another, and, where i) the first conductive electrodes and ii) the second conductive electrodes form a two-dimensional configuration.

20 Claims, 25 Drawing Sheets

(56) References Cited

U.S. PATENT DOCUMENTS

| | | |
|---|---|---|
| 2013/0236882 A1 | 9/2013 | Yu et al. |
| 2014/0323350 A1 | 10/2014 | Nguyen et al. |
| 2016/0025610 A1 | 1/2016 | Katsumoto et al. |
| 2019/0128726 A1* | 5/2019 | Zorzetto ............... G01F 23/268 |

OTHER PUBLICATIONS

W. Q. Yang et al.,"Electrical capacitance tomography with square sensor," Electronics Letters, vol. 35, No. 4, 1999, pp. 295-296.

T. N. Phua et al., "Weak-inversion measurement circuit for miniature electrical capacitance tomography," IEEE Transactions on Instrumentation and Measurement, vol. 57, No. 2, 2008, pp. 379-385.

D. De Venuto et al., "Design of an integrated low-noise read-out system for DNA capacitive sensors." 2nd International Workshop on Advances in Sensors and Interface, IWASI, 2007, 6 pages.

"Modeling and simulation of multi-plane Electrical Capacitance Tomography sensor for flow imaging by using Finite Element Analysis" Areeba Shafquet; I. Ismail; Azuraien Jaafar 2014 5th International Conference on Intelligent and Advanced Systems (ICIAS) Year: 2014, pp. 1-6.

"Capacitance Planar Array Sensor for Fast Multiphase Flow Imaging" Sebastian Thiele; Marco Jose Da Silva; Uwe Hampel IEEE Sensors Journal Year: 2009, vol. 9, Issue: 5, pp. 533-540.

\* cited by examiner

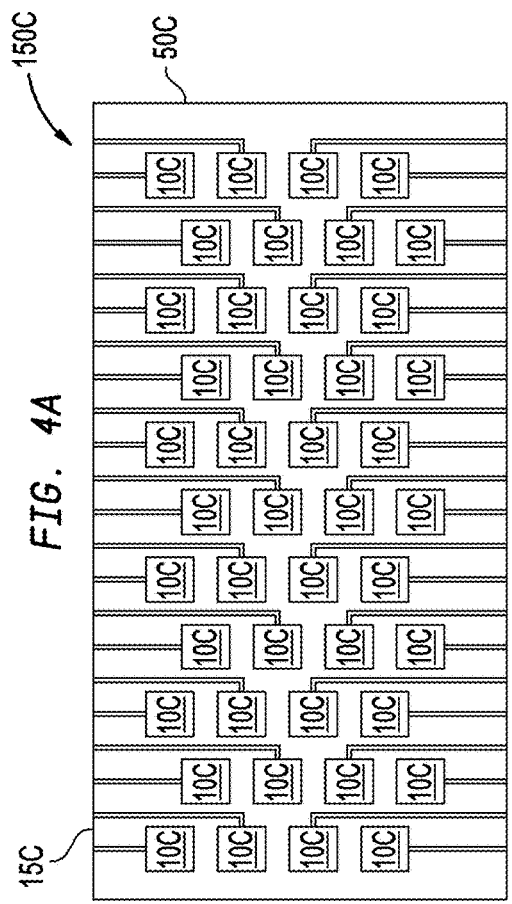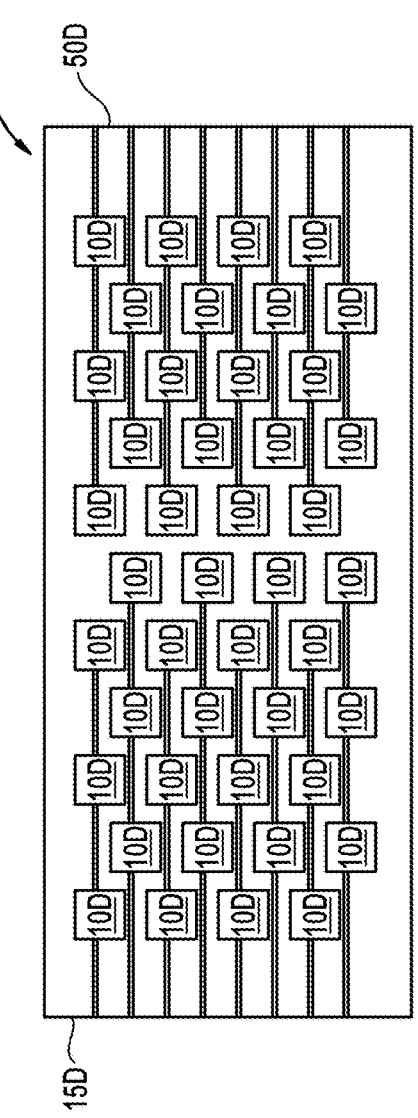

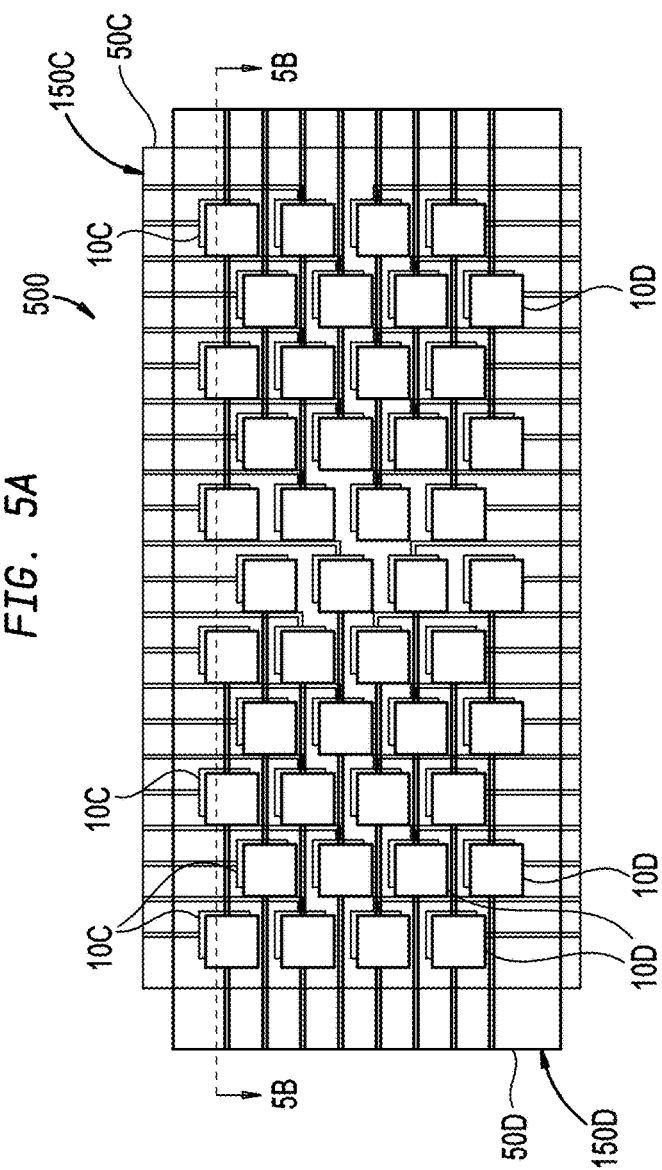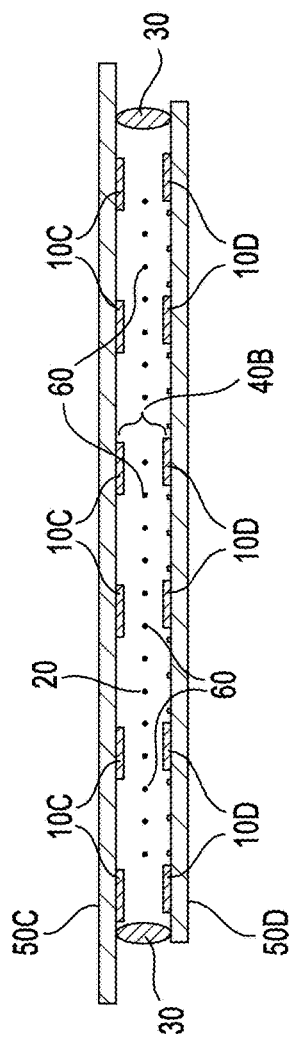

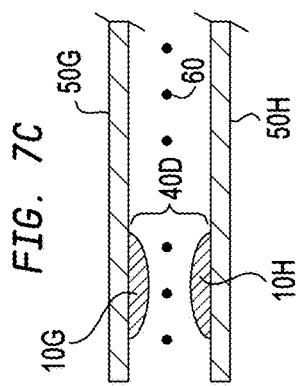
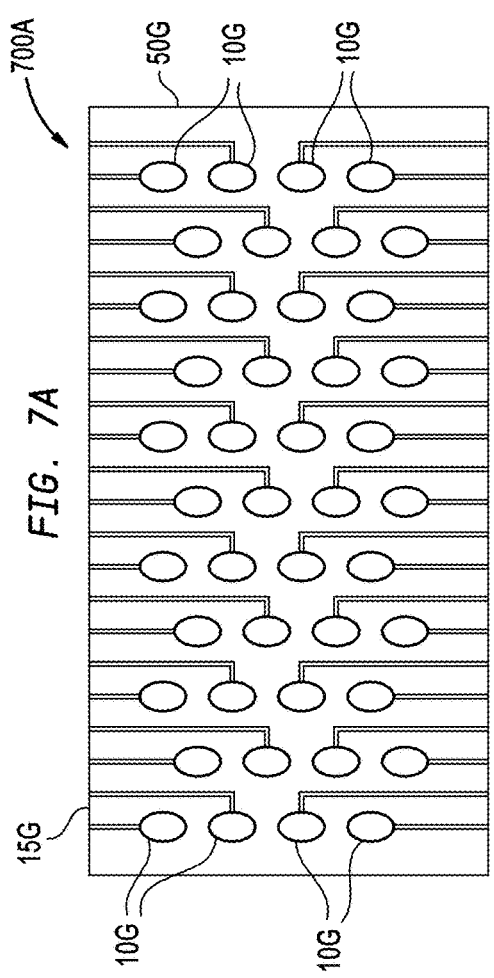
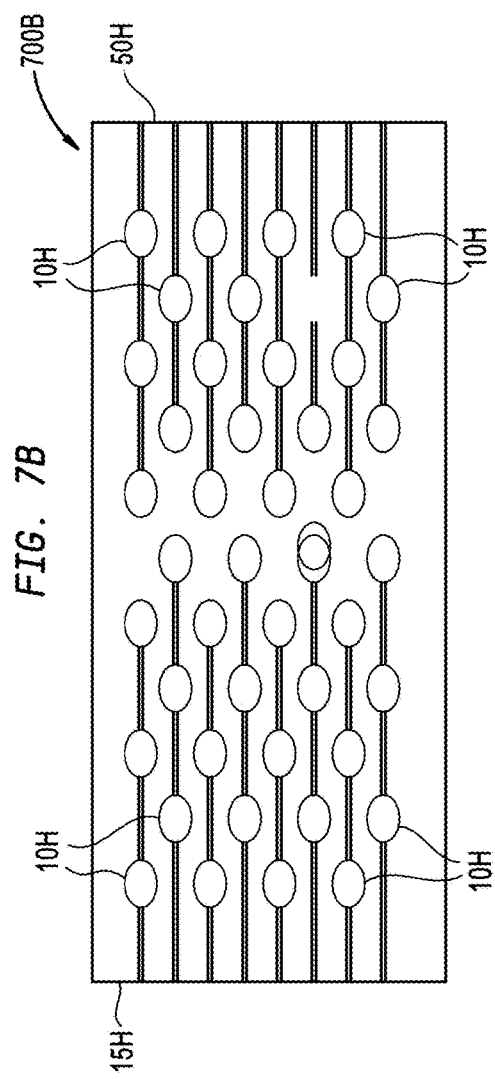

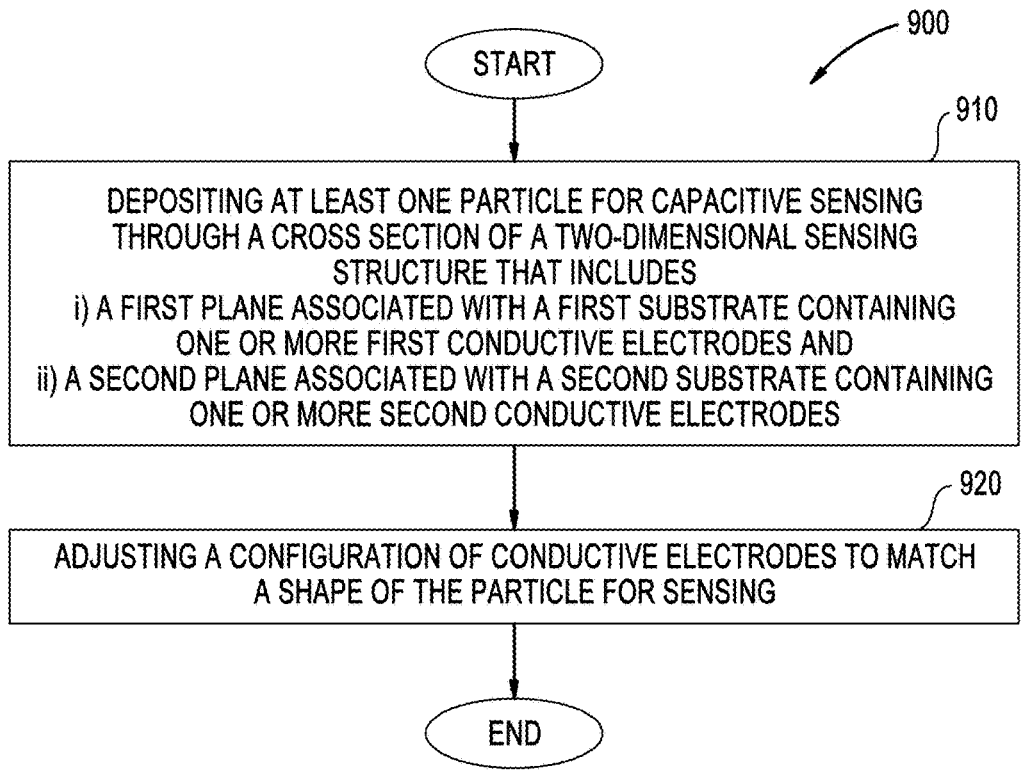
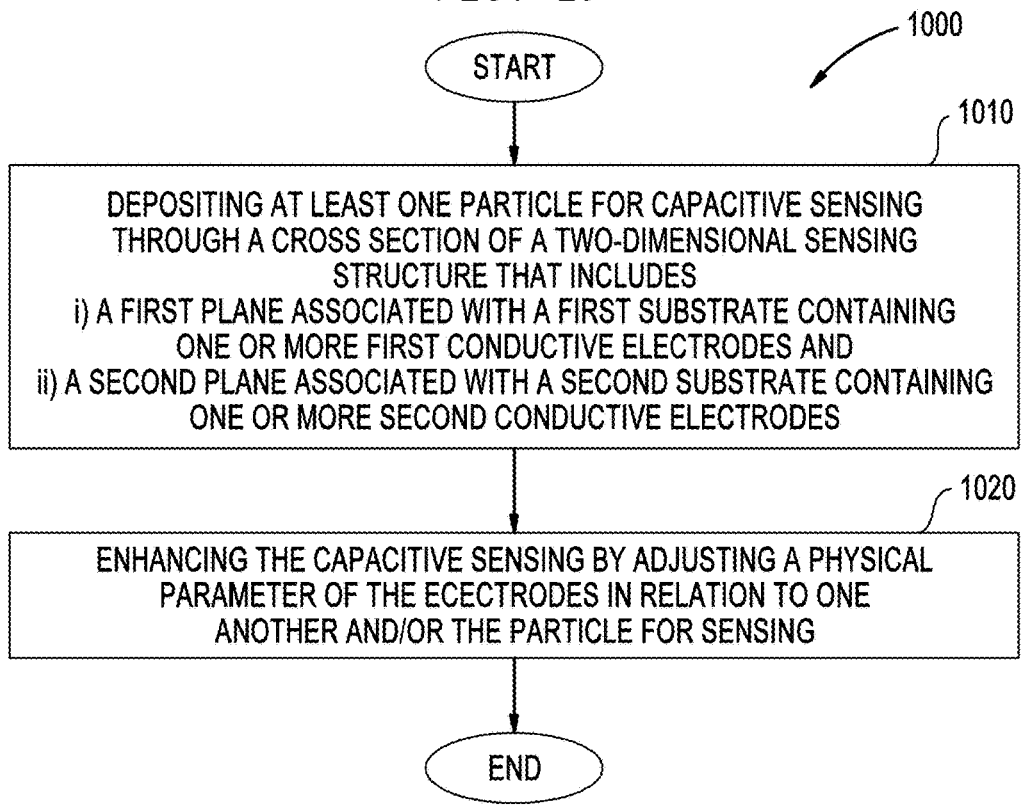

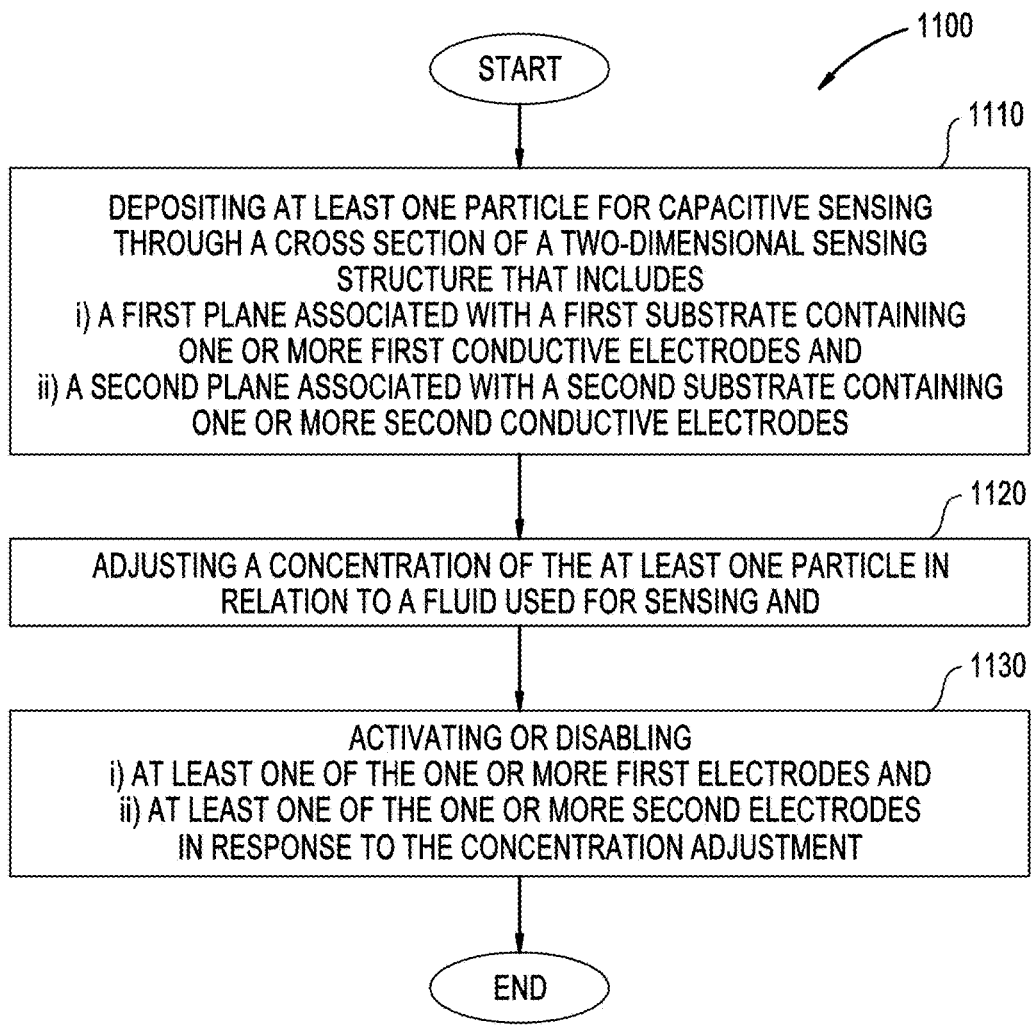

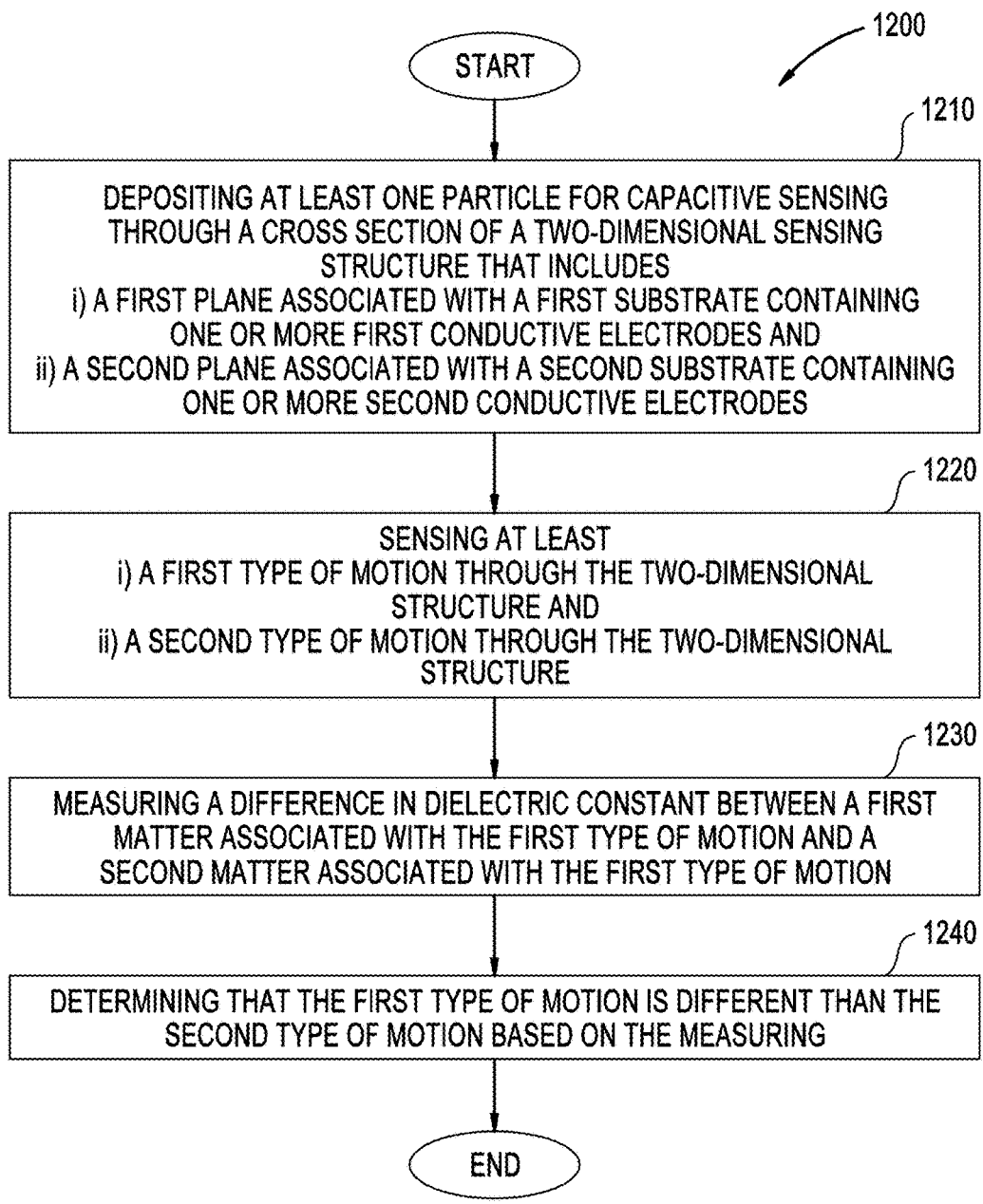

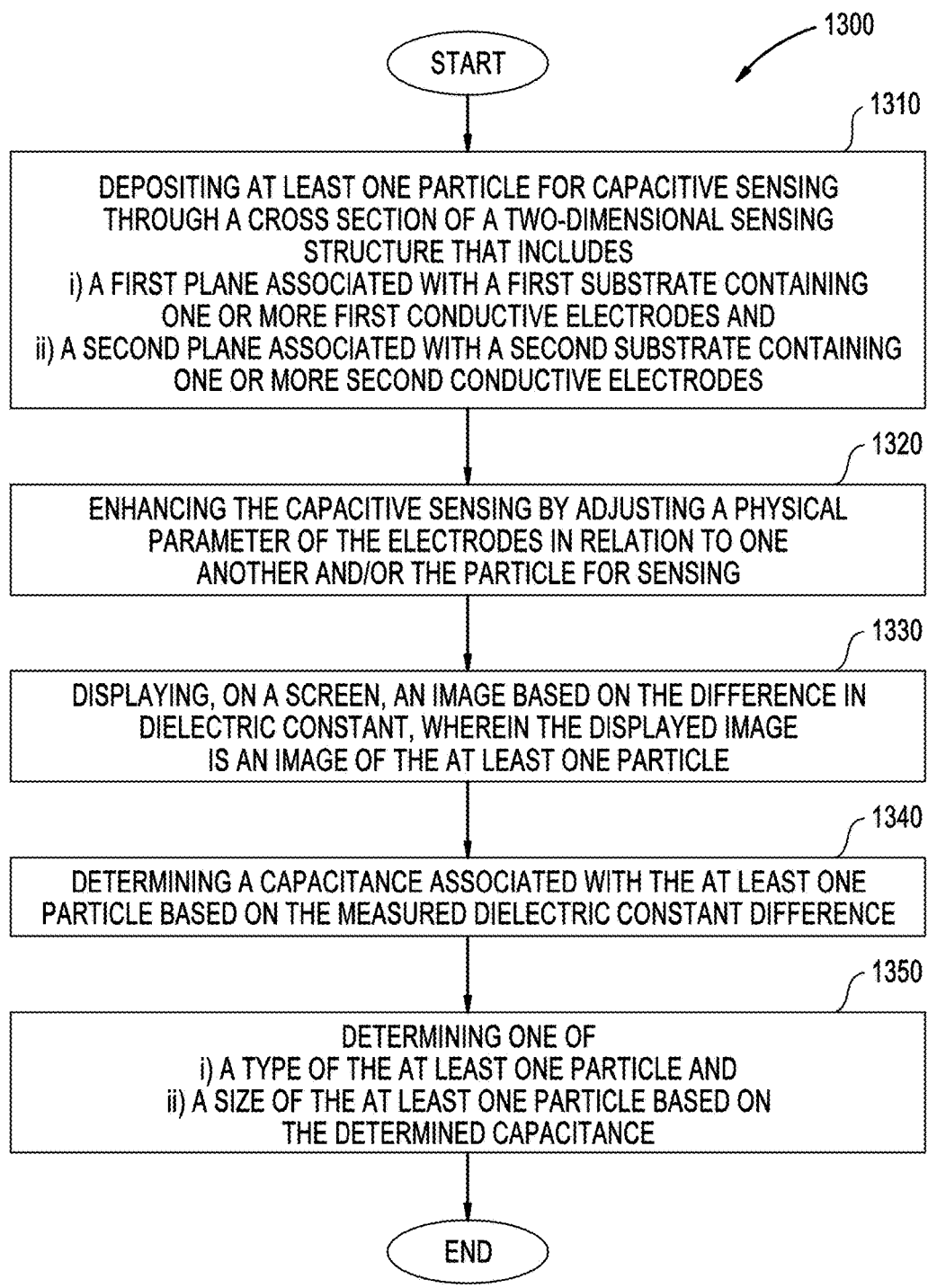

FIG. 14

```
                    START
                      │
                      ▼
┌─────────────────────────────────────────────────┐ ─ 1410
│ DEPOSITING BIOLOGICAL AGENT FOR CAPACITIVE      │
│ SENSING THROUGH A CROSS SECTION OF A            │
│ TWO-DIMENSIONAL SENSING STRUCTURE THAT INCLUDES │
│ i) A FIRST PLANE ASSOCIATED WITH A FIRST        │
│ SUBSTRATE CONTAINING ONE OR MORE FIRST          │
│ CONDUCTIVE ELECTRODES AND                       │
│ ii) A SECOND PLANE ASSOCIATED WITH A SECOND     │
│ SUBSTRATE CONTAINING ONE OR MORE SECOND         │
│ CONDUCTIVE ELECTRODES                           │
└─────────────────────────────────────────────────┘
                      │
                      ▼
┌─────────────────────────────────────────────────┐ ─ 1420
│ COMBINING THE BIOLOGICAL AGENT WITH ANOTHER     │
│ SUBSTANCE                                       │
└─────────────────────────────────────────────────┘
                      │
                      ▼
                  ╱ 1430 ╲
         NO    ╱    DID    ╲
      ◄─────  ╱  SUBSTANCE   ╲
              ╲  AFFECT BIO  ╱
               ╲   AGENT?   ╱
                ╲          ╱
                    │ YES
                    ▼
┌─────────────────────────────────────────────────┐ ─ 1440
│ IDENTIFYING A TYPE OF THE BIOLOGICAL AGENT IF   │
│ THE SUBSTANCE AFFECTED THE BIOLOGICAL AGENT     │
└─────────────────────────────────────────────────┘
                      │
                      ▼
                    END
```

1400

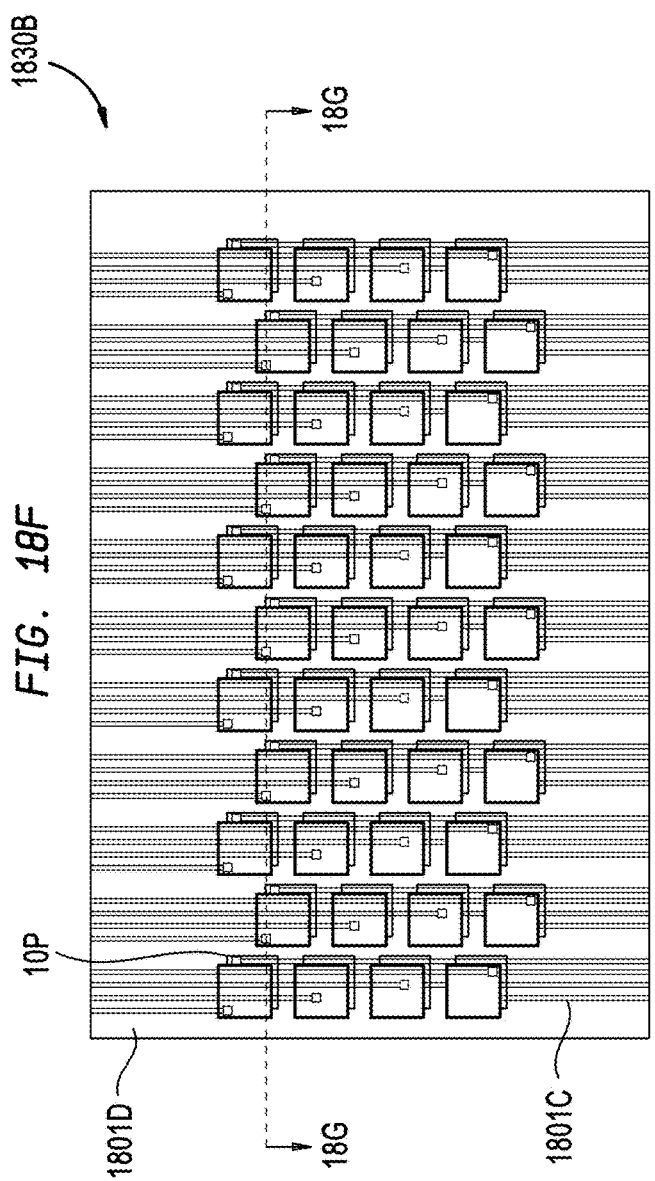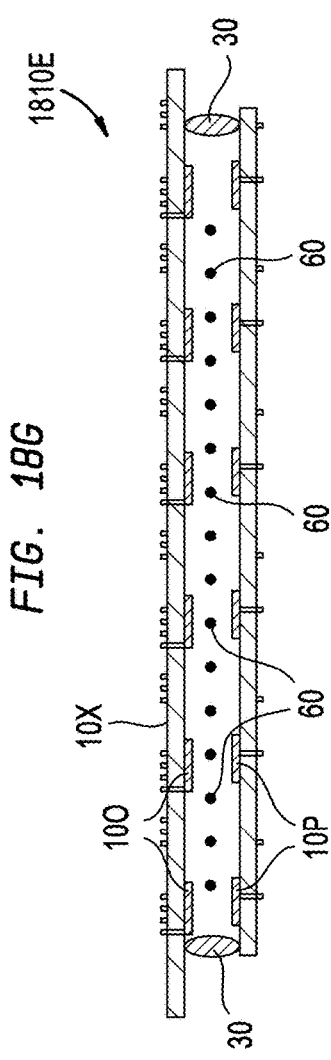

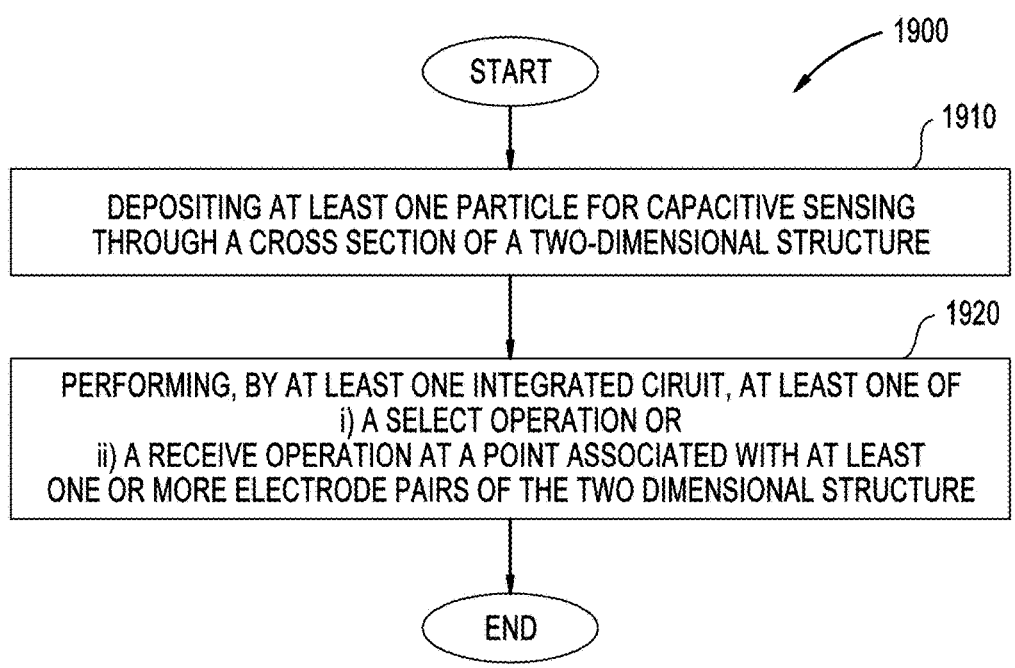

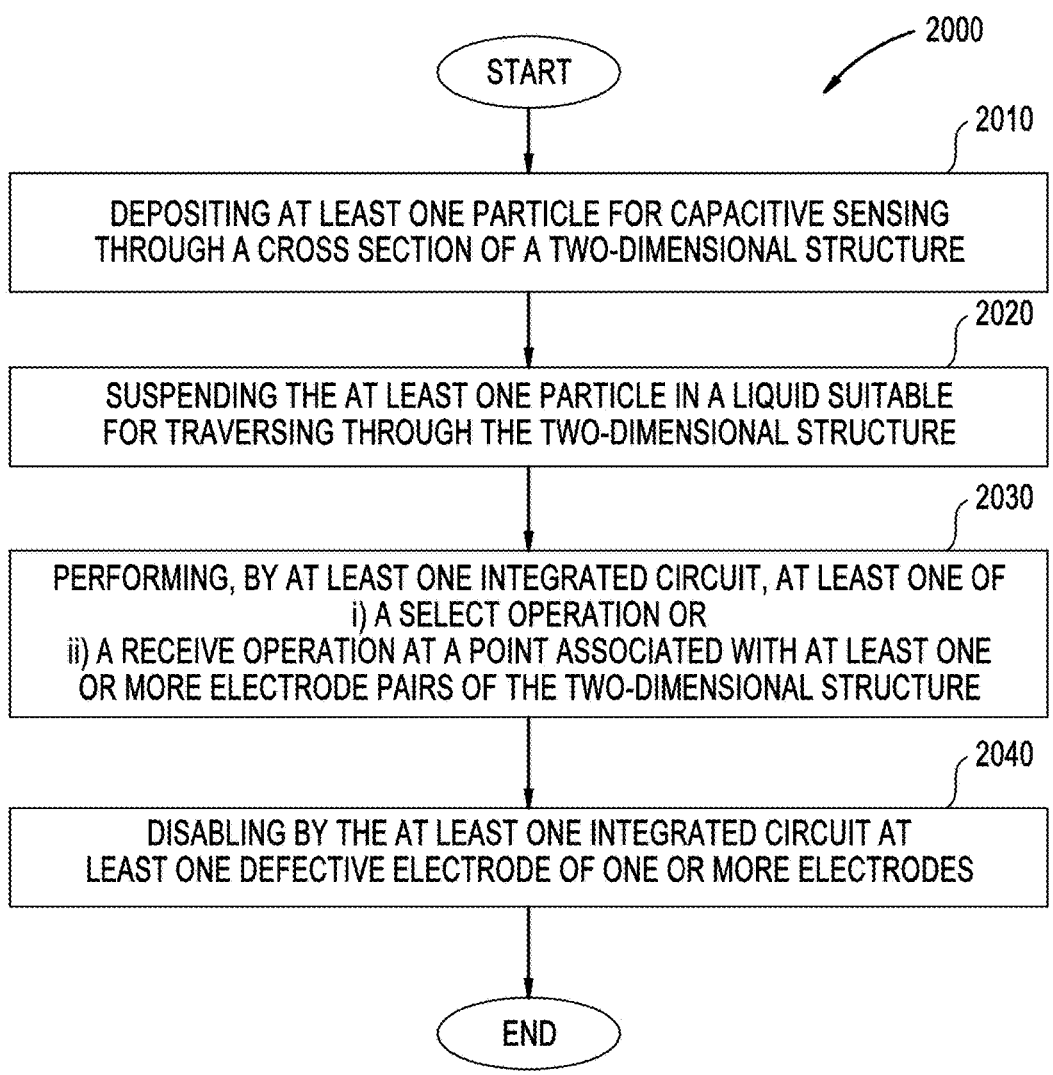

… least one of i) a select operation or ii) a receive operation at a point associated with at least one of the one or more electrode pairs.

According to another embodiment of the present disclosure a method for sensing is provided. The method includes: depositing at least one particle for capacitive sensing through a cross section of a two-dimensional structure, where the two-dimensional structure includes: i) a first plane associated with a first substrate containing one or more first conductive electrodes and ii) a second plane associated with a second substrate containing one or more second conductive electrodes, where the one or more first conductive electrodes and the one or more second electrodes are overlapping with respect to one another, and where the i) one or more first conductive electrodes and ii) the one or more second conductive electrodes form a two-dimensional sensing configuration, connecting, respectively, the one or first conductive electrodes to one or more first conductive lines by one or more first vias, and connecting, respectively, the one or second conductive electrodes to one or more second conductive lines by one or more second vias, where each one of the one or more first electrodes and each corresponding one of the one or more second electrodes forms one or more electrode pairs configured to receive at least one particle for sensing.

BRIEF DESCRIPTION OF THE SEVERAL VIEWS OF THE DRAWINGS

FIG. 4A illustrates a structure useful for two-dimensional (2-D) capacitive sensing in accordance with at least one embodiment of the present disclosure.

FIG. 4B illustrates a structure useful for two-dimensional (2-D) capacitive sensing in accordance with at least one embodiment of the present disclosure.

FIG. 5A illustrates a two-dimensional (2-D) capacitive sensing structure in accordance with at least one embodiment of the present disclosure.

FIG. 5B illustrates a sensing cross-section of a two-dimensional (2-D) capacitive sensing structure in accordance with at least one embodiment of the present disclosure.

FIG. 6A illustrates a structure useful for two-dimensional (2-D) capacitive sensing in accordance with at least one embodiment of the present disclosure.

FIG. 6B illustrates a structure useful for two-dimensional (2-D) capacitive sensing in accordance with at least one embodiment of the present disclosure.

FIG. 7A illustrates a structure useful for two-dimensional (2-D) capacitive sensing in accordance with at least one embodiment of the present disclosure.

FIG. 7B illustrates a structure useful for two-dimensional (2-D) capacitive sensing in accordance with at least one embodiment of the present disclosure.

FIG. 7C illustrates a sensing cross-section of a two-dimensional (2-D) capacitive sensing structure in accordance with at least one embodiment of the present disclosure.

FIG. 9 illustrates a method for two-dimensional (2-D) capacitive sensing in accordance with at least one embodiment of the present disclosure.

FIG. 10 illustrates a method for two-dimensional (2-D) capacitive sensing in accordance with at least one embodiment of the present disclosure.

FIG. 11 illustrates a method for two-dimensional (2-D) capacitive sensing in accordance with at least one embodiment of the present disclosure.

FIG. 12 illustrates a method for two-dimensional (2-D) capacitive sensing in accordance with at least one embodiment of the present disclosure.

FIG. 13 illustrates a method for two-dimensional (2-D) capacitive sensing in accordance with at least one embodiment of the present disclosure.

FIG. 14 illustrates a method for two-dimensional (2-D) capacitive sensing in accordance with at least one embodiment of the present disclosure.

FIG. 18F illustrates a two-dimensional (2-D) sensing structure that is useful for two-dimensional (2-D) capacitive sensing, where the structure includes at least one via connection useful for dimensional (2-D) capacitive sensing, in accordance with at least one embodiment of the present disclosure.

FIG. 18G illustrates a sensing cross-section of a two-dimensional (2-D) sensing structure that is useful for two-dimensional (2-D) capacitive sensing, where the structure includes at least one via connection useful for dimensional (2-D) capacitive sensing, in accordance with at least one embodiment of the present disclosure.

FIG. 19 illustrates a method for two-dimensional (2-D) capacitive sensing in accordance with at least one embodiment of the present disclosure.

FIG. 20 illustrates a method for two-dimensional (2-D) capacitive sensing in accordance with at least one embodiment of the present disclosure.

DETAILED DESCRIPTION

Figure 1:
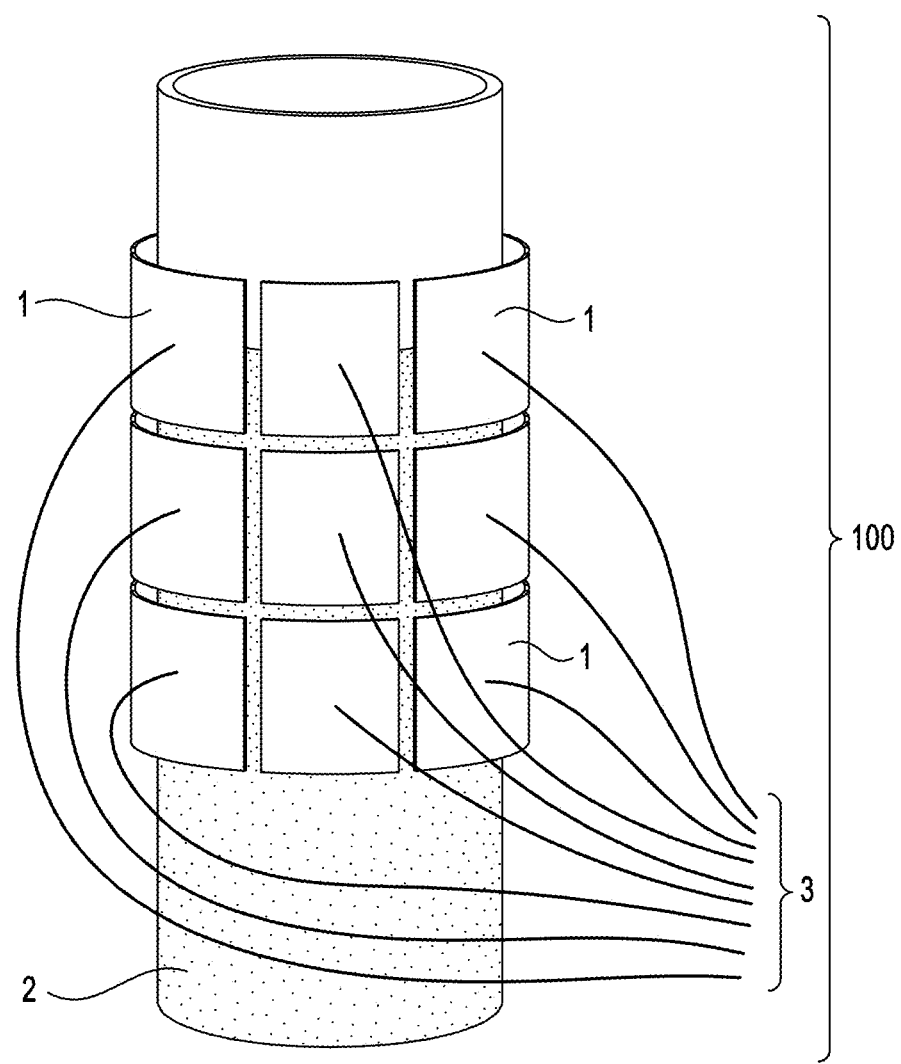
FIG. 1 illustrates a 3-D cylindrical sensing structure as is known in the art.

The sensitivity matrix of a capacitance sensor is a map of capacitance variations with respect to a set of discrete dielectric perturbations that can be translated into an imaging domain. The capacitance of the sensor depends on the dielectric permittivity of the medium between the pair of capacitor sensor electrodes, where the actual capacitance (Ca) of a particle part of a fluid sample, such as a liquid sample with a particle contained therein, is in series with a substrate capacitance, such as a 2D glass (or other material) noted as a slide capacitance (Cs). A particle can be any chemical or material constituent contained in a fluid, such as a liquid medium. One example of a particle is a bio-agent, e.g. virus or bacteria, in a liquid that can be transmitted through a sensing device.

The total capacitance (Ct) of the sensor can be expressed as:

$$C_t = \frac{C_a C_s}{(C_a + C_s)} \quad \text{(Equation 1)}$$

The capacitance of the slide material, e.g. the glass (or other material), is dependent on the dielectric material of the glass (or other material) and is a constant, while the actual capacitance due to a liquid sample is proportional to the dielectric constant of the liquid and solid filling the volume between the two material slides.

The effective permittivity ($\epsilon_a$) of the host liquid and particles, e.g. nanoparticle(s), contained therein depends on the volume percentage of the two, and can be expressed as:

$$\epsilon_a = (V_l \epsilon_l + V_p \epsilon_p)/V_t \quad \text{(Equation 2)}$$

Where Vl, Vp, Vt is the volume of the liquid, the particles, e.g. a nanoparticles, and the total volume, respectively, and $\epsilon_l$, $\epsilon_p$ are the dielectric permittivity of the liquid particles, respectively.

If the sensor electrodes are in direct contact with the liquid sample (not the two-dimensional slide or substrate), then the total Capacitance is simply:

$$C_t = C_a = \epsilon_a A/d \quad \text{(Equation 3)}$$

(Where A/d correlate to the separation between the electrodes of an electrode pair.)

The above relationships can contribute to formulating one or more structures, systems, and methods for capacitive sensing for particles contained in a fluid medium, including a liquid medium, that are transported through, e.g. the liquid medium contains the particle and transmits it through a sensing structure, at least two planes or surfaces forming a two-dimensional capacitive structure. One or more physical parameters of the i) transporting fluid medium, ii) the electrodes and/or conductive lines used for sensing, and iii) the configuration of the electrodes used for sensing can be adjusted to enhance the ability to detect particles transported through the structure. In one or more embodiments, the two-dimensional structure can overcome problems associated with detecting bio-particles in a capacitance sensing scheme, and in one embodiment, more particularly, problems associated with detecting small bio-particles, e.g. less than or equal to 200 nm, are overcome.

Figure 2A:
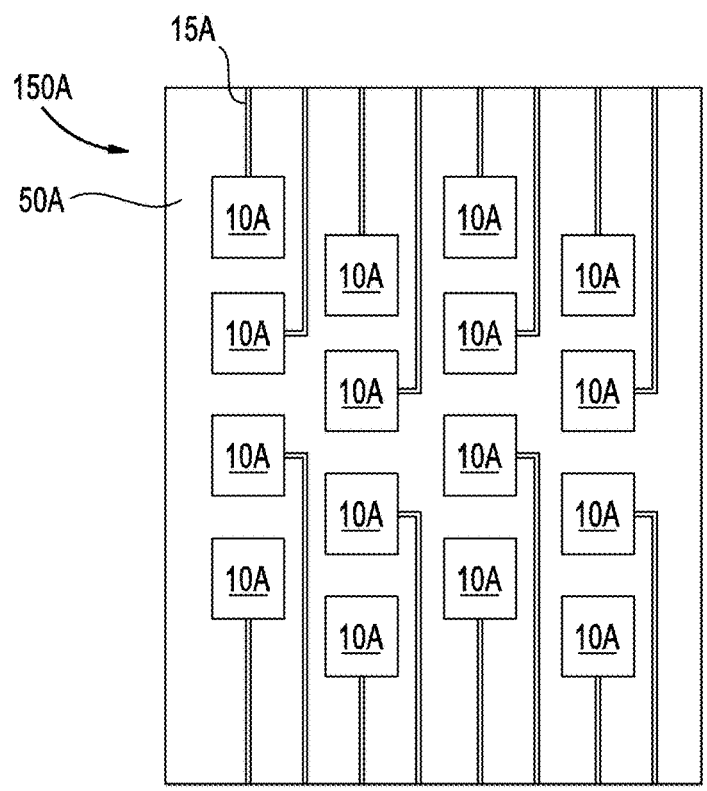
FIG. 2A illustrates a structure useful for two-dimensional (2-D) capacitive sensing in accordance with at least one embodiment of the present disclosure.

FIG. 2A illustrates a structure 150A, which includes substrate 50A with one or more electrodes 10A according to an embodiment of the present disclosure. The substrate 50A can include glass, plastic, organic printed circuit boards or any other material or composition suitable as a substrate for containing an electrode 10A and for detecting a change in an electrical property of a surrounding medium as a result of a material deposited thereon or material coming in proximity thereto. The one or more electrodes 10A can include any material suitable for conducting electricity or detecting a chance in an electrical property, including metals and/or semiconductor materials, including silver (Ag), copper (Cu), gold (Au), or aluminum (Al), indium tin oxide (ITO), fluorine doped tin oxide (FTO), and doped zinc oxide (ZnO). In one embodiment, the one or more electrodes 10A have one or more conductive lines 15A connecting the one or more electrodes 10A to and from the substrate 50A. The one or more conducting lines 15A can be any suitable material for conducting electricity including a metal such as gold, aluminum, copper, silver, etc.

Figure 2B:
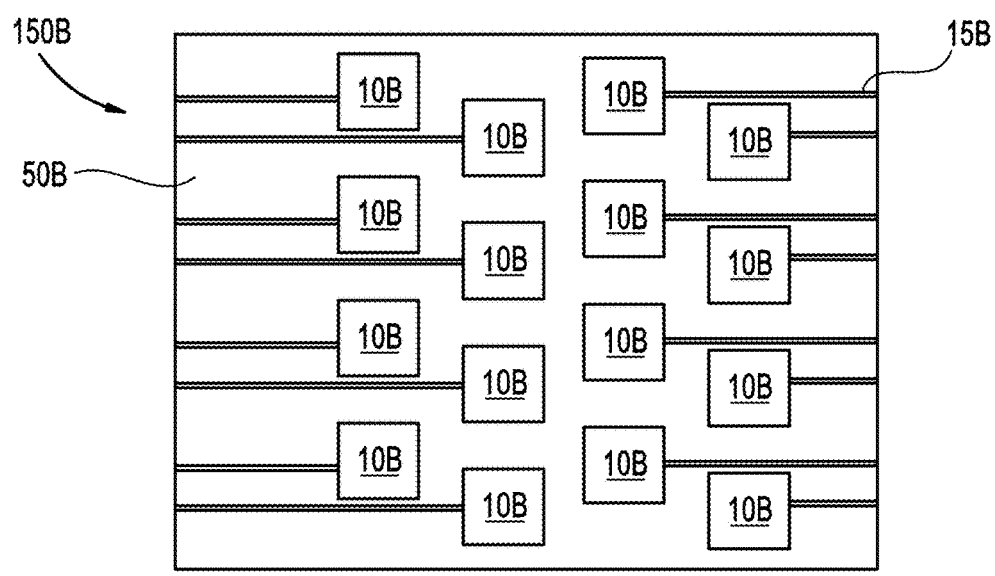
FIG. 2B illustrates a structure useful for two-dimensional (2-D) capacitive sensing in accordance with at least one embodiment of the present disclosure.

As in FIG. 2A, FIG. 2B illustrates a structure 150B, which includes substrate 50B with one or more electrodes 10B according to an embodiment of the present disclosure. The substrate 50B can include glass, plastic, organic printed circuit boards or any other material or composition suitable as a substrate for containing an electrode 10B and for detecting a change in an electrical property of a surrounding medium as a result of a material deposited thereon or material coming in proximity thereto. The one or more electrodes 10B can include any material suitable for conducting electricity or detecting a chance in an electrical property, including metals and/or semiconductor materials, including silver (Ag), copper (Cu), gold (Au), or aluminum (Al), indium tin oxide (ITO), fluorine doped tin oxide (FTO), and doped zinc oxide (ZnO). In one embodiment, the one or more electrodes 10B have one or more conductive lines 15B connecting the one or more electrodes 10B to and from the substrate 50B. The one or more conducting lines 15B can be any suitable material for conducting electricity including a metal such as gold, aluminum, copper, silver, etc.

Figure 2C:
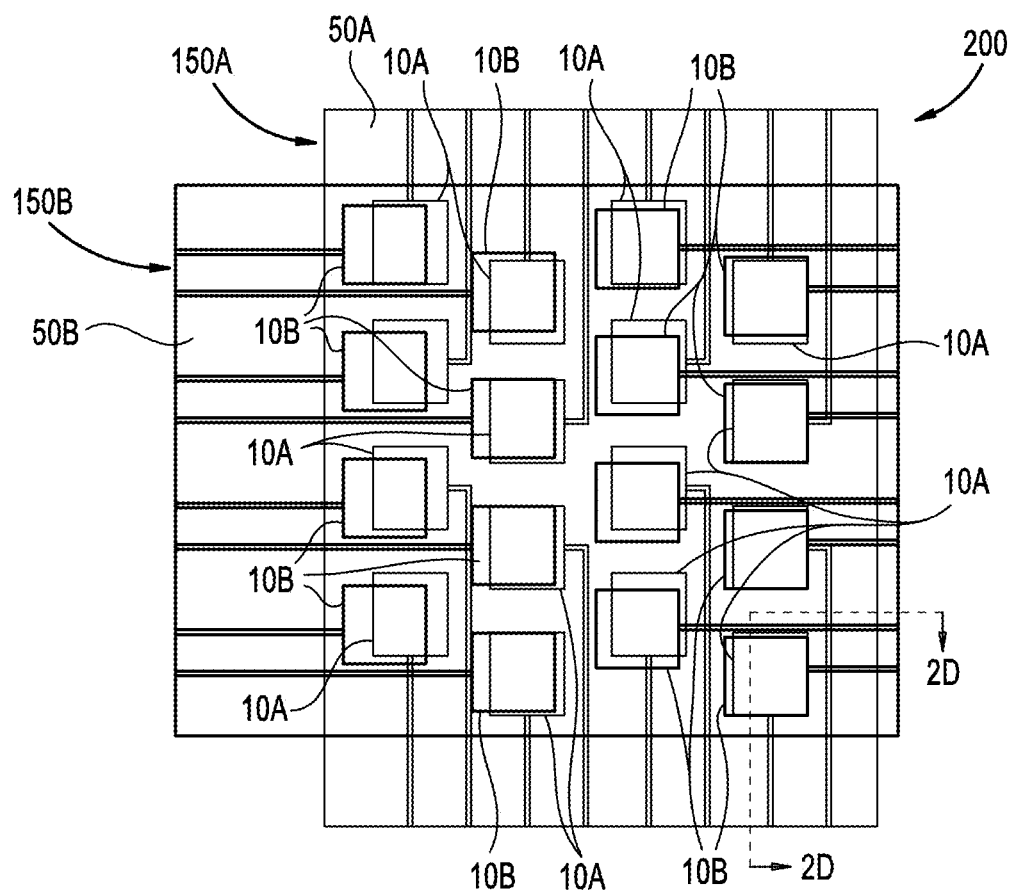
FIG. 2C illustrates a two-dimensional (2-D) capacitive sensing structure in accordance with at least one embodiment of the present disclosure.
Figure 15A:
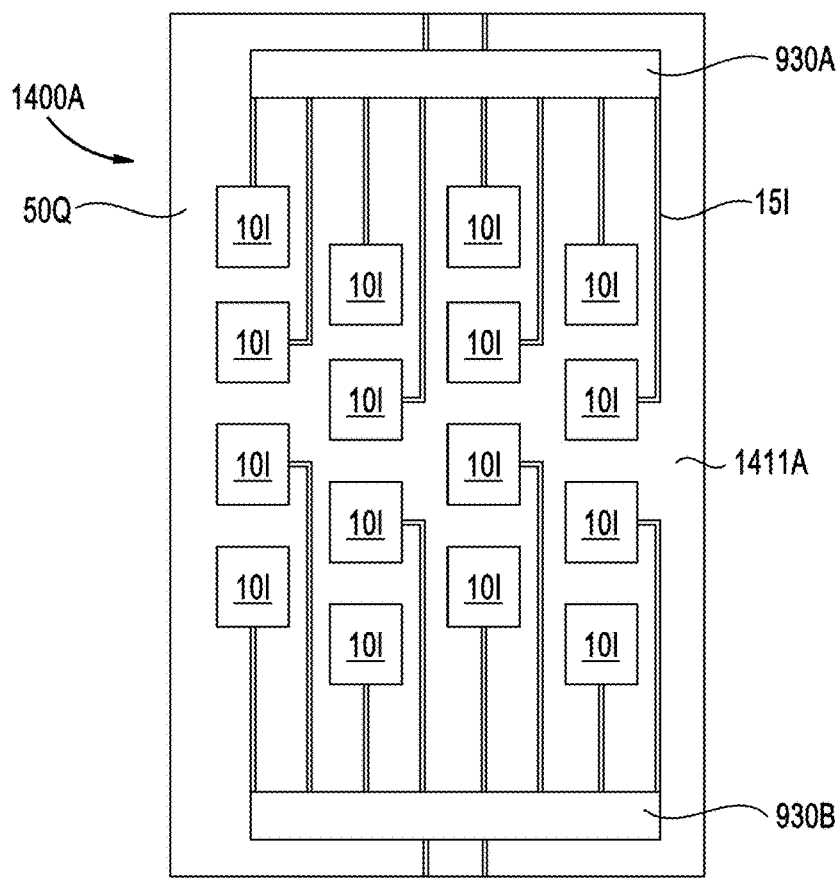
FIG. 15A illustrates a structure that is useful for two-dimensional (2-D) capacitive sensing, where the structure includes at least one integrated circuit useful for dimensional (2-D) capacitive sensing, in accordance with at least one embodiment of the present disclosure.
Figure 15B:
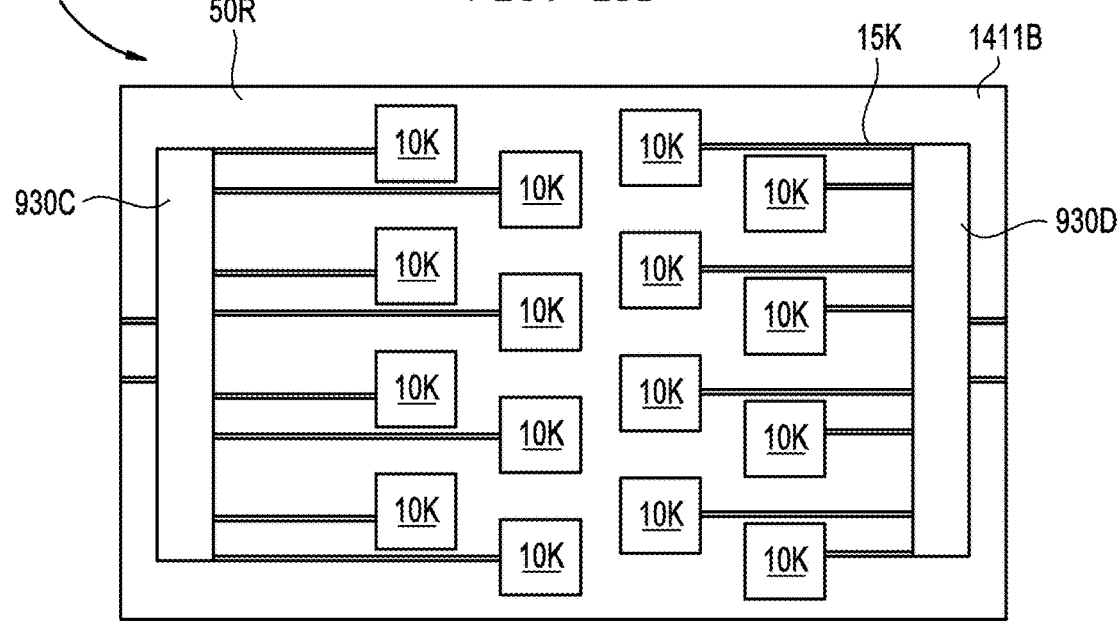
FIG. 15B illustrates a structure that is useful for two-dimensional (2-D) capacitive sensing, where the structure includes at least one integrated circuit useful for dimensional (2-D) capacitive sensing, in accordance with at least one embodiment of the present disclosure.

FIG. 2C illustrates a two-dimensional structure 200 for capacitive sensing (referred to herein interchangeably as a two-dimensional sensing structure, two-dimensional electrode structure, or two-dimensional electrode sensing structure), where the structure includes overlapping substrate 50A and substrate 50B such that they form parallel planes or surfaces in relation to one another, and such that the electrodes, e.g., 10A, of one plane or surface do not physically contact the electrodes, e.g. 10B, of another plane or surface. According to one embodiment, the one or more conductive lines 15A, 15B can be arranged so that they enable the one or more electrodes 10A, 10B to have a uniform distribution on each respective substrate, e.g. 50A, 50B, and to have a uniform distribution once overlaid on top of one another as shown in FIG. 2C. (Note that for clarity, in FIG. 2C, 15A, 15B are not expressly label, the location of the conductive lines is understood from FIG. 2A and FIG. 2B). In one embodiment, as shown, this can be accomplished by having, in one substrate, e.g. 50A, the one or more conducting lines 15A connecting the one or more electrodes 10A in a top down fashion, e.g. the one or more conducting lines 15A connecting to each electrode 10A by extending from the top or bottom of the substrate 50A, and having the one or more conductive lines 15B of the other substrate 50B connect to each one of the one or more electrodes 10B laterally, e.g. from one or more sides of the substrate 50B. In other words, pursuant to one embodiment, the one or more conductive lines 15A, 15B have a distinct arrangement with respect to one another. In another embodiment, as discussed below, the arrangement can be the same. In one embodiment, the overlaid capacitors 10A, 10B form one or more capacitors (as discussed below) with respect to one another. In one embodiment, there are one or more dielectric materials (not shown) between the one or more substrates 50A, 50B. As shown, the one or more electrodes on each plane or surface are physically disconnected from the electrodes of the other plane or surface, e.g. the one or more electrodes of substrate 50A and the one or more electrodes of 50B, e.g. do not physically contact electrodes in the same plane and/or electrodes on different plane, and the electrodes can be electrically insulated from one another in the same plane or surface and with respect to the electrodes on the other plane or surface, by selecting a substrate with high insulating properties, such as glass, or depositing an insulator material, such as polyimide, between a substrate that is not necessarily insulating, and the respective electrodes to be physically isolated electrically.

Figure 2D:
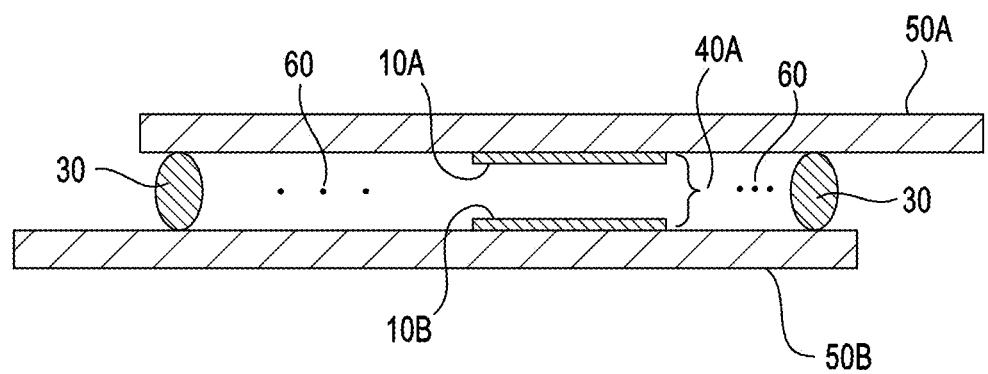
FIG. 2D illustrates a sensing cross-section of a two-dimensional (2-D) capacitive sensing structure in accordance with at least one embodiment of the present disclosure.

FIG. 2D illustrates a cross-section of the two-dimensional structure 150C taken along the section lines shown in FIG. 2C. A gasket or spacer 30 sealing top and bottom substrates has an opening (void of gasket or spacer material not shown) into which a particle or particles contained in a fluid medium is disposed between the substrates 50A, 50B for capacitive sensing. The particle or particles in a fluid medium disposed between the substrates 50A and 50B exhibit motion over time through a channel 20 which is formed by overlapping the two substrates 50A, 50B, and an electrode pair 40A is formed by electrode 10A overlapping electrode 10B and forming a cross section as a result of the overlapping. In one embodiment, the electrode pair 40A can be a capacitor formed by the alignment. In one embodiment, there are one or more dielectric materials (not shown) in between the one or more substrates 50A, 50B. In the embodiment of FIG. 2D, a uniform configuration is shown, e.g. the top and bottom electrode 10A, 10B are substantially aligned over one another and the spacing between each electrode pair is substantially the same and/or each substrate has a pattern with respect to a set of electrodes that repeats itself, e.g. a particular pattern configuration appears more than once on the substrate. The particle(s) 60 can be contained in a fluid (not shown) and carried through the channel 20 by the fluid, or it can be brought to the entry of the channel, and then flow through the channel as a result of dimensional configurations (as discussed below). As the particle(s) 60 moves through the channel 20, the electrodes sense a change in capacitance and detection of the particle can be accomplished. In one embodiment particles of different of different size and constitution can flow through the channel. As discussed below, in one embodiment, dimensional adjustments can be made to adjust the sensing propensity and functionality.

The resulting structure FIG. 2D offers various advantages for capacitive sensing, e.g. it minimizes cross talk between electrodes and conductive lines as a result of the parallel and planar configuration. Furthermore, it allows a user to configure and/or select one or more of the following: i) electrode shape, ii) the gap between the one or more electrodes 10A, 10B, iii) dielectric properties of the electrodes and material therebetween in order to better detect one or more particles that are deposited through the electrode for capacitive sensing, iv) the type of fluid used to facilitate the transmission, and v) the concentration of fluid in relation to the particle. For example, in one embodiment, the electrode shape can be selected to approximate or match the shape of a particle to be deposited in a channel between the one or more substrates 50A, 50B. In one embodiment, a gap distance between the first plane or surface and the second plane or surface of the substrate 50A and the substrate 50B is greater than the spacing between at least two of the one or more electrodes 10A in the first plane or surface and at least two of the one or more electrodes 10B in the second plane or surface. In one embodiment, the spacing between the electrodes in each plane or surface can be adjusted to decrease or increase the frequency of measurements and/or reduce the impact of the measurements. In one embodiment, the gap between the substrates 50A, 50B can be adjusted or selected to be narrower than one dimension, e.g. width, length, or height of the particle(s) 60 that will flow through the channel 20; this ensures a tight travel area for the particle, and increases the chance of isolating a capacitance change associated with the particle(s) 60, as opposed to noise, interference, or changes associated with other substances, as the particle travels through an electrode pair 40. In one embodiment, the gap between the substrates 50A, 50B can be adjusted so that, if the particle(s) 60 is contained in a liquid, only the particle will flow through the channel, with minimal or no liquid flowing there through. In one embodiment, restricting the particle movement by selecting and/or adjusting the width, length, or height of the channel 20 to be narrower than the particle(s) 60 allows the measurement simplification of reducing the particle motion to one or more dimensions along the channel, which can be a reduction from a three-dimensional motion travel to a two-dimensional channel, or even a one-dimensional motion travel. This can enhance motion by reducing the area for sensing and for minimizing interferences from other sources. Although not expressly shown there can be difference in particle size. It should be noted that the channel 20 can have more than one particle and/or particle type and/or particle size or it can one particle type and/or particle size for sensing. For the purposes of this disclosure, references may be made to one particle or the other, without intending to limit an embodiment to that specific particle in relation to the other.

Adopting one or more features of any of the above embodiments further minimizes cross talk issues associated with the electrodes and conductive lines associated therewith and/or minimizes physical interference with detecting the particle(s) 60. The above embodiments are useful for general applications and for particles of all sizes, but can offer a particular advantage when dealing with bio-particles, e.g. viruses, bacteria, antibodies, and cells, where those bio-particles are less than or equal to 200 nm. The reason the above embodiments can offer such an advantage is that the size, volatility, and vulnerability of bio-particles of such a size can make detection difficult due to i) cross-talk, ii) physical changes of the particle during transmission, iii) noise, and/or iv) influences by the carrying medium, e.g. carrying liquid, and the two-dimensional structure above mitigates some of all of the adverse influences associated with these and other adverse issues. Furthermore, the techniques and structures disclosed herein an offer the ability to detect the particles down to a single particle.

Figure 3:
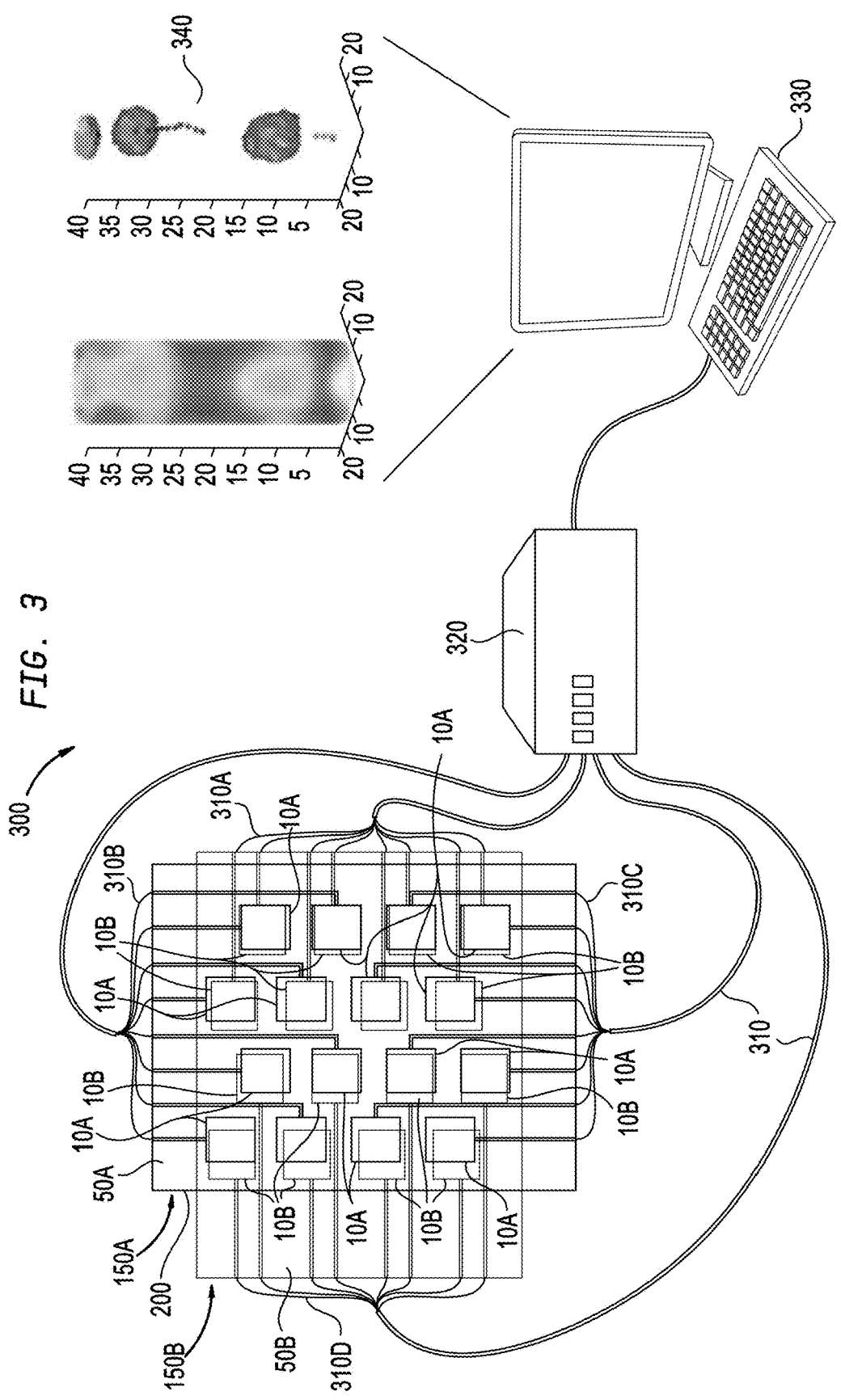
FIG. 3 illustrates a two-dimensional (2-D) capacitive sensing system in accordance with at least one embodiment of the present disclosure.

FIG. 3 includes a two-dimensional sensing system 300, which includes, in accordance with one of the embodiments of the present disclosure, e.g. 200, or equivalent a two-dimensional sensing structure 200 connected to a multiple sensing circuit and/or instrumentation device 320, which in turn connects to a computer device 330 with a display. The multiple sensing circuit 320 connects to the two-dimensional structure, e.g. 200, by having one or more wires 310, which split into a plurality of wires 310A, 310B, 310C, 310D, each connected to a conductive line on the one or more substrates of the structure 200, which in turn means that the system connects directly to each electrode of the structure 200. The multiple sensing circuit(s) 320 can receive instructions from the computer device, or be independently programmed by a user, to enable or disable any one of the electrodes of the structure 200 as a result of the connection establishes the plurality of wires 310A, 310B, 310C, 310D. The computer device 330 can be equipped with a display device that can display an image 340 associated with the detected particle 60 based on the changes in capacitance detected by the one or more electrodes of the structure. In one embodiment, where a fluid, such as a liquid, is employed to transmit the one or more particles 60 through the channel 20, the one or more electrodes will detect a different capacitance change when the fluid transmits through the channel, as opposed to the particle. Since the dielectric constant of the liquid differs from the dielectric constant of the one or more particles 60, and since by extension the capacitance is directly related to the dielectric constant, the system can determine when fluid is being transmitted through the channel as opposed to the one or more particles 60 by comparing capacitance measurements as the fluid and one or more particles travels through the cross-section and are detected, respectively, by the one or more electrode pairs 40. The sensing circuit 320 can read this information from the structure, and can transmit this to the computer device 330, which can present an image, including a moving image which correlates with the motion of the fluid and one or more particles, as discussed in greater detail below, on the display.

FIGS. 4A, 4B, and 5A illustrate structures 150C, 150D forming a two-dimensional sensing structure 500 that is useful for two-dimensional sensing in accordance with the present disclosure, where the sensing structure is formed from the structures 150C, 150D to form a staggered electrode configuration. Structures 150C, 150D include, respectively, a substrate 50C and 50D, with one or more electrodes 10C and 10D. As above, the substrate 50C, 50D can include glass, plastic, organic printed circuit boards or any other material or composition suitable as a substrate for containing an electrode and for detecting a change in an electrical property of a surrounding medium as a result of a material deposited thereon or material coming in proximity thereto. As above, the one or more electrodes 10C, 10D can include any material suitable for conducting electricity or detecting a chance in an electrical property, including metals and/or semiconductor materials, including silver (Ag), copper (Cu), gold (Au), or aluminum (Al), indium tin oxide (ITO), fluorine doped tin oxide (FTO), and doped zinc oxide (ZnO). In one embodiment, the one or more electrodes 10C, 10D have one or more conductive lines 15C, 15D connecting one another in the respective substrates 50C, 50D such that when the substrates 50C, 50D are overlaid over one another to form the overlaid structure as shown, the resulting structure has at least one electrode pair 40B with a staggered configuration (shown in FIG. 5B). In other words, there is an offset between one or more electrode 10C and one or more electrode 10D, which can be formed by a fabrication process in which a first set of electrodes, e.g. electrodes 15C, is formed on a first plane and a second set of electrodes e.g. electrodes 15C, is formed on a second and parallel plane, where the respective electrodes of an electrode pair are misaligned on their respective center axes. In one embodiment, this staggered configuration is shown by the conductive line formations 150C, 150D as arranged with respect to one another in structure 500. As above, the conductive lines 15C, 15D can be any suitable material for conducting electricity including a metal such as gold, aluminum, copper, silver, etc.

FIG. 5B illustrates a cross section of the structure formed by structures 150C of structure 150D. As above, the particle is deposited through a channel 20 which is formed by overlapping the two substrates 50C, 50D, and an electrode pair 40B is formed by electrode 10C overlapping electrode 10D. In one embodiment, the electrode pair 40B can be a capacitor formed by the alignment. In one embodiment, there are one or more dielectric materials (not shown) in between the one or more substrates 50C, 50D. As above, the particle 60 can be contained in a fluid (not shown) and carried through the channel 20 by the fluid, or it can be brought to the entry of the channel, and then flow through the channel as a result of dimensional configurations (as discussed below). As the particle 60 moves through the channel 20, the electrodes sense a change in capacitance and detection of the particle can be accomplished. One advantage of the staggered configuration can be an enhanced ability to detect fast moving and/or small particle, e.g. less than 200 nm, as a result of a repeat delay pattern that can be observed due to the offset between the one or more electrodes 10C, 10D of each one or more electrode pair 40B. This can offer an additional benefit for bio-particles that can change shape or velocity as they transmit through the channel 20 and/or influenced by transmission medium, e.g. the fluid carrying the bio-species particle and/or other noise and interference associated with the detection process.

Figures 6A, 6B:
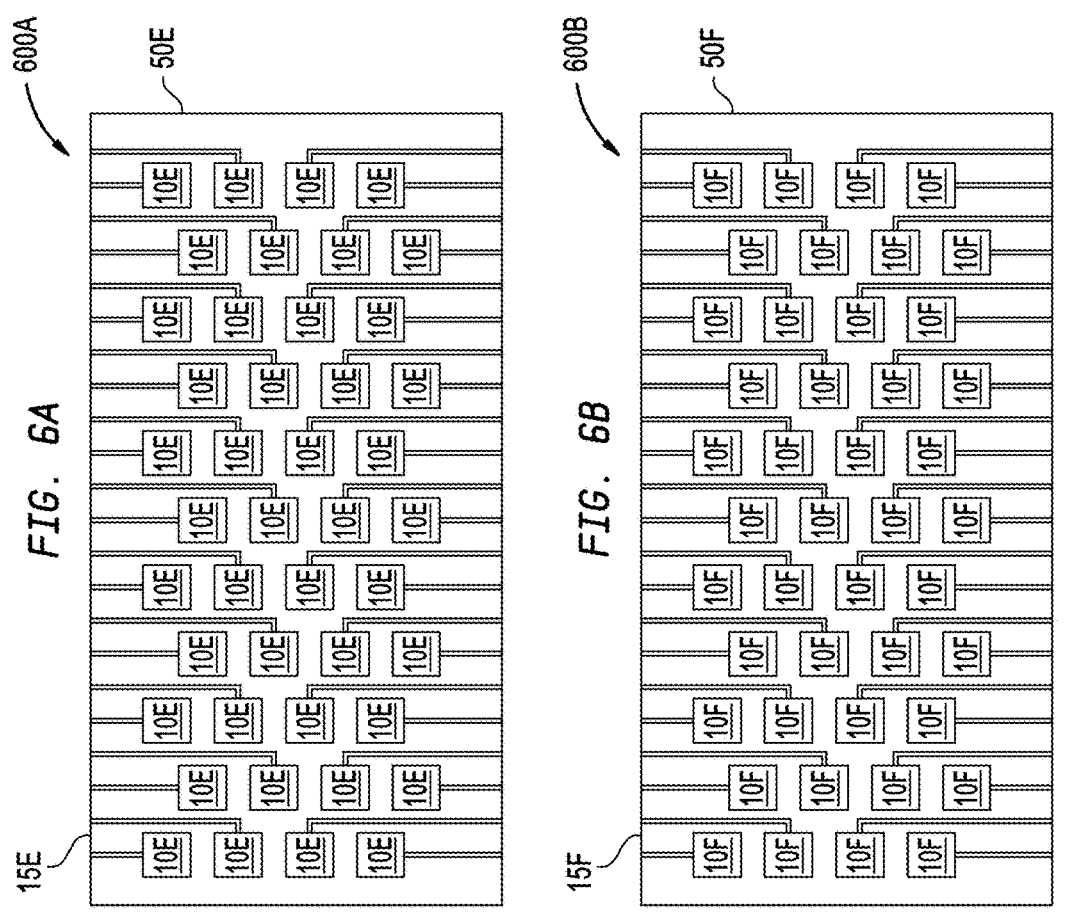

FIG. 6A and FIG. 6B illustrate structures, respectively, 600A and 600B. The structures include substrates 50E and 50F, respectively, which in turn include one or more electrodes 10E and 10F, respectively. The structure further includes, respectively, conductive lines 15E and 15F that are used to connect the one or more electrodes 10E and 1F on the substrates 50E and 50F. In this embodiment, the substrates 50E and 50F have a matching electrode configuration, which can be used to form a two-dimensional electrode structure (not shown). The resulting electrode structure can take on a configuration that is congruent with the matching electrode configuration on each substrate 50E and 50F, and in accordance with the teachings of the present disclosure, including that at least one pair of electrodes form a capacitor that can detect a particle flowing through a channel between the two substrates, where the channel is formed by overlaying the two substrates 50E and 50F. One advantage of this configuration, in addition to other advantages expressly stated or implied by the present disclosure, is that the manufacturing process for making the structures 600A and 600B can be streamlined, as two different electrode configurations, and by extension conductive line configurations, is not required. In one embodiment, another advantage, per one embodiment, is that capacitance area sensed by electrode pair overlap (such as electrode pairs 40B) can be made scaled small enough to scale to an infinitesimally small particle, e.g. 60, as the capacitance area overlap is not dependent on the electrode 10A and 10B, or 10C and 10D, but only dependent on the alignment of substrate 50A to 50B, or substrate 50C to 50D, where the respective electrode pair overlap dictates the capacitance area sensed.

FIG. 7A illustrates a structure 700A, which includes substrate 50G with one or more electrodes 10G according to an embodiment of the present disclosure. The substrate 50G can include glass, plastic, organic printed circuit boards or any other material or composition suitable as a substrate for containing an electrode 10G and for detecting a change in an electrical property of a surrounding medium as a result of a material deposited thereon or material coming in proximity thereto. The one or more electrodes 10G can include any material suitable for conducting electricity or detecting a chance in an electrical property, including metals and/or semiconductor materials, including silver (Ag), copper (Cu), gold (Au), or aluminum (Al), indium tin oxide (ITO), fluorine doped tin oxide (FTO), and doped zinc oxide (ZnO). In one embodiment, the one or more electrodes 10G have one or more conductive lines 15G connecting the one or more electrodes 10G to and from the substrate 50A. The one or more conducting lines 15G can be any suitable material used for forming conductive lines.

As shown in FIG. 7A, the electrodes 10G are selected to approximate the shape of an incoming particle(s) 60, shown in the cross section FIG. 7C. When the structure 700A is overlaid with structure 700B, which has one or more electrodes 10H and one or more conductive lines 15H, where the one or more electrodes of structure 700B also approximate the shape of the incoming particle(s) 60, a more accurate sensing can take place as the shape of the particle will better conform to the one or more electrode pairing 40D as shown in FIG. 7C. The conductive line configurations 15H and 15G are selected to be from different directions, but other configurations are possible. As shown, per one embodiment, the conductive line configuration 15H shows several electrodes 10H connected in series while the conductive line configuration 15G shows one electrode 10G connected to each conductive line configuration.

It should be stated that the above and below configurations are non-limiting and other configurations are possible in accordance with the teachings of the present disclosure.

Figure 8:
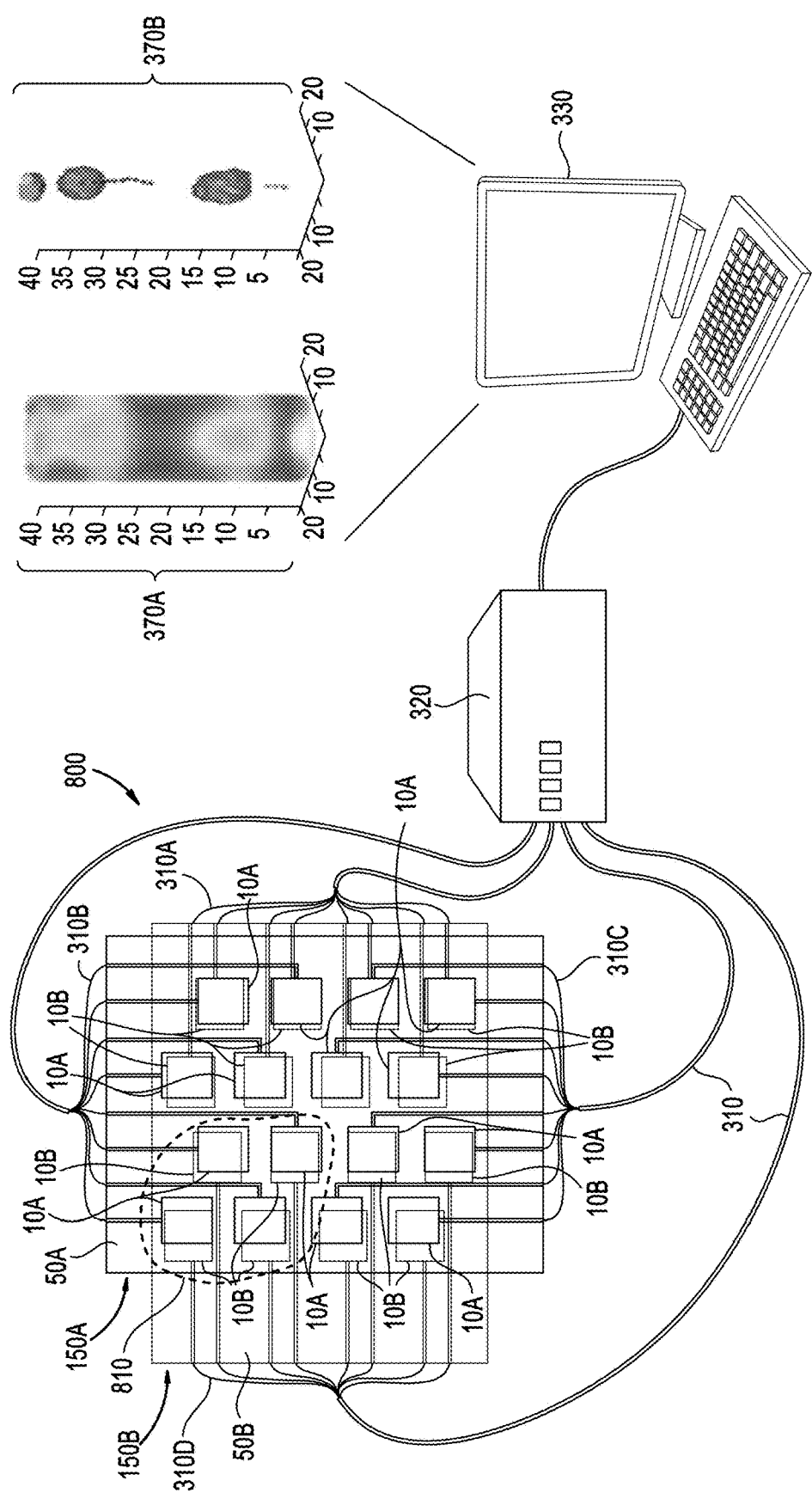
FIG. 8 illustrates a two-dimensional (2-D) capacitive sensing system in accordance with at least one embodiment of the present disclosure.

FIG. 8 includes a two-dimensional sensing system 800, similar to the sensing system 300 shown in FIG. 3. The computer device 330 can select one or more electrodes 800 to approximate a shape of a particle 60 to be deposited through the cross-section of a two-dimensional sensing structure, e.g. the sensing structure 200 shown in FIG. 2d. The multiple sensing circuit 320 connects to the two-dimensional structure, e.g. sensing structure 200, by having one or more wires 310, which split into a plurality of wires 310A, 310B, 310C, 310D, each connected to a conductive line on the one or more substrates of the structure 200. As a result, the system connects directly to each electrode of the structure 200. The multiple sensing circuits 320 can receive instructions from the computer device, or be independently programmed by a user, to enable or disable any one of the electrodes of the structure 200 as a result of the connection established by the plurality of wires 310A, 310B, 310C, 310D. The multiple sensing circuits can enable or disable one or more of the electrodes of the structure 200 to correlate to a particular physical attribute of the one or more particle, e.g. 60, to be deposited through the structure 200, including enabling one or more electrode pairs 810 to approximate the shape of the one or more particle 60 to be deposited through the two-dimensional structure 200, to accommodate a particular dimension associated with the one or more particle 60, e.g. if a dimension size in one direction makes sensing more practical, electrodes can be selected or disabled based on this basis, and/or, as discussed below, to accommodate a known motion pattern or velocity trajectory of a particular particle 60 deposited through the structure 200. The computer device 330 can be equipped with a display device that can display an image 370A, 370B associated with the detected particle 60 based on the changes in capacitance detected by the one or more electrodes of the structure.

The two-dimensional structures disclosed above and anywhere else herein, and equivalents which can be manufactured in accordance with the teachings of the present disclosures, can be in various methods for establishing capacitive sensing.

FIG. 9 illustrates a method for detecting a particle transmitted through a two-dimensional sensing structure according to an embodiment of the present disclosure. The two-dimensional structure or system as illustrated in any of the structures and systems of the present disclosure, including structure 200, system 300, structure 500A, etc. In 910, a particle is deposited through a cross section of i) a first plane or surface associated with a first substrate containing one or more first conductive electrodes and ii) a second plane or surface associated with a second substrate containing one or more second conductive electrodes, where a capacitor is formed between the one or more first conductive electrodes and the one or more second conductive electrodes. The two-dimensional structure or system can have the properties of at least one of the structures or systems described above, including the first plane or surface and a second plane or surface, and by extension the electrodes associated with each plane or surface, being parallel to one another and physically and electrically insulated from one another. In one embodiment, per 920, the one or more electrodes of at least one of the substrates can be adjusted or selected to match the shape of the particle to be deposited through the two-dimensional structure. For example, a system, as system 300, can be used to select one or more electrodes in a manner that approximates the shape of the particle to be deposited through the channel of the two-dimensional structure, e.g. 200, connected to the system. In another embodiment, the shape of the actual electrode of a two-dimensional sensing structure, as shown in FIGS. 7A and 7B, is selected to match the shape of a particle to be deposited through the structure 200. This embodiment can offer a particular advantage when detecting a small bio-particle, such as a virus or bacterium less than or equal to 200 nm, as a matching shape between the electrode and the bio-particle will enhance chance of detecting a change in capacitance as a result of the bio-particle traveling through an electrode pair, as opposed to another change, such as the transmission medium, e.g. the liquid carrying the bio-particle. As mentioned above, in one embodiment, other electrode pair embodiments may match the shape of particle, e.g. bio-particle, by having the alignment of the electrode pair overlap area (rather than the electrode shape itself) match the shape of the bio-particle.

FIG. 10 illustrates a method 1000 for detecting a particle transmitted through a two-dimensional sensing structure according to an embodiment of the present disclosure. As above, the two-dimensional structure or system as illustrated in any of the structures and systems of the present disclosure, including structure 200, system 300, structure 500A, etc. In 1010, a particle is deposited through a cross section of i) a first plane or surface associated with a first substrate containing one or more first conductive electrodes and ii) a second plane or surface associated with a second substrate containing one or more second conductive electrodes, where a capacitor is formed between the one or more first conductive electrodes and the one or more second conductive electrodes. The two-dimensional structure or system can have the properties of at least one of the structures or systems described above, including the first plane or surface and second plane or surface, and by extension the electrodes associated with each plane or surface, being parallel to one another and physically and electrically insulated from one another. In 1020, in addition to selecting the shape of one or more electrodes in relation to a particle to be deposited through a cross section of the two-dimension structure, e.g. 200, other physical parameters associated with the electrodes can be adjusted to enhance sensing of a deposited particle. For example, the gap between one or more electrodes may be adjusted so that only the deposited particle can be transmitted there through, as opposed to other different particles in conjunction within the transmission fluid, or the gap can be selected so that it matches one dimension of a particle to be deposited there through, effectively acting like a mechanical filter and permitting a more isolated screening and contact with the particle of a certain size or dimension, and by extension, superior sensing. For example, if a particular bio-particle, such as a virus that is particularly small, e.g. Dengue virus which has a size of approximately 50 nm in one direction, is deposited through the cross section of the structure, then the gap between the electrode pair can be selected to match or approximately match that dimension to permit a better sensing of that virus by prohibiting other material from flowing through the channel as the virus or bio particle travels there through. In one embodiment, such as when a system, e.g. 300, is used to carry out one or more steps of the method, multiple electrode pairs can be disabled or activated in response to the size of the particle, e.g. in a two-dimensional scheme n/2 of measurements are possible, where n represents the total number of independent electrodes, and for a particularly small particle, a maximum number of activations can occur so as to obtain repeat detections through the system as the particle moves, which distinguish the detection of the one or more particle as opposed to noise or capacitance changes stemming from other materials.

FIG. 11 illustrates a method 1100 for detecting a particle transmitted through a two-dimensional sensing structure according to an embodiment of the present disclosure. As above, the two-dimensional structure or system as illustrated in any of the structures and systems of the present disclosure, including structure 200, system 300, structure 500A, etc. In 1110, a particle is deposited through a cross section of i) a first plane or surface associated with a first substrate containing one or more first conductive electrodes and ii) a second plane or surface associated with a second substrate containing one or more second conductive electrodes, where a capacitor is formed between the one or more first conductive electrodes and the one or more second conductive electrodes. The two-dimensional structure or system can have the properties of at least one of the structures or systems described above, including the first plane or surface and second plane or surface, and by extension the electrodes associated with each plane or surface, being parallel to one another and physically and electrically insulated from one another. In 1120, a concentration of fluid or other physical parameter associated with a fluid, e.g. viscosity for liquid, in relation to the one or more particles to be deposited through the two-dimensional sensing structure, e.g. 200, is adjusted. The adjustment can be reducing the concentration of the one or more particles to be transmitted through the cross channel of a two-dimensional device or increasing the concentration of the one or more particles through the cross channel of the two-dimensional structure. As the one or more particles travels through the channel, repeat capacitance measurements can be obtained that correlate to the one or more particle, as opposed to the fluid or other materials. In one embodiment, per 1130, the electrodes can be activated or disabled based on the concentration by a system configuration, e.g. 300, such that, for example, when a low concentration of particles is delivered through the cross section of the two-dimensional structure, more electrodes are activated to increase the number of obtained measurements, and when a high concentration of particles is delivered through the cross section of the two-dimensional structure, more electrodes are disabled to sparse out the measurements and ensure detected capacitance changes are due to the one or more particles as opposed to other factors.

FIG. 12 illustrates a method 1200 for detecting a particle transmitted through a two-dimensional sensing structure according to an embodiment of the present disclosure, where the method includes at least one step using motion characteristics of one or more particles to make an identification or determination with respect to the same.

According to one embodiment, the underlying techniques associated with Brownian motion are used to enable the determination. Particles, including particles less than or equal to 200 nm, can be identified by the nature of their movement, which in turn can be determined by Brownian motion principles. For example, Analyte particles, e.g. nanoparticles, including bio-particles, undergoing Brownian motion can be governed by the following expression in two dimensions:

$$\delta x^2 = 4Dt \quad \text{(Equation 4)}$$

(which gives the mean-square displacement of the particle in terms of its diffusion constant 'D' in the liquid medium as a function of observation time 't')

From above the time for observation for a particle with diffusion coefficient estimated with a given area of the electrode, A as follows:

$$t_{obs} = \delta x^2 / 4D = A/4D \quad \text{(Equation 5)}$$

"A" is defined as the active capacitive electrode area, "na" is defined as the number of analyte molecule, e.g. nanoparticles, per unit volume. Pursuant to this relationship, it is possible to detect a signal due to the presence of tens to hundreds of molecules using a single sensor. However, in a typical scenario, with nanoparticles that are particularly large, it would take an unacceptably long time (Dt~large) for an analyte molecule to come transit from one electrode area into another electrode area (to detect motion). The above scenario can be overcome by employing one or more electrodes, such as an array of small electrodes distributed over space operating in parallel and in a two-dimensional sensing structure as described in one or more embodiments of the present disclosure. In one embodiment, for n/2 array of paired electrodes working in parallel, e.g. in a two-dimensional sensing structure, the corresponding detection time is roughly scaled down by 2/n, retaining the sensitivity amount of time for collection the information from all the array elements. In one embodiment, were there are n/2 electrode pairs, there are n connections, or alternatively, n/m detection circuits, where m refers to the number of multiplex occurrences.

Referring once again to FIG. 12, per 1210, one or more particles are transmitted through a two-dimensional sensing structure, e.g. 200. A computer device, e.g. 330, of a system, e.g. 300, connected to the two-dimensional sensing structure can be configured pursuant to a Brownian motion scheme to intake one or more measurements from the two-dimensional sensing structure and determine a particular type of motion, by comparing it to multiple capacitance measurements, occurring over a given time. In one embodiment, per 1220, a first type of motion can be sensed, e.g. a motion associated with a change in capacitance as a result of the one or more particles, and a second type of motion can be sensed, e.g. a motion associated with another material or substance deposited through the two-dimensional structure, such as a fluid transmitting the one or more particles. In one embodiment, per 1230, the dielectric constant is measured or determined with respect to the one or more particles and the other material, e.g. the fluid transmitting the one or more particles. Since the other parameters are constant, e.g. the physical dimensions of the channel, the difference in capacitance can be attributed to the difference in dielectric constants of the measured materials, e.g. the one or more particles and the deposited fluid transmitting the one or more particles. Per 1240, since the difference in capacitance correlates to a difference in motion, and visa-versa, the computer device can determine a difference between the first motion and the second motion, and then identify the material or a physical parameter associated with a material based on the motion.

FIG. 13 illustrates a method 1300 for detecting a particle transmitted through a two-dimensional sensing structure according to an embodiment of the present disclosure. As above, the two-dimensional structure or system as illustrated in any of the structures and systems of the present disclosure, including structure 200, system 300, structure 500A, etc. Per 1310, one or more particles are transmitted through a two-dimensional capacitive sensing structure, e.g. 200. In one embodiment, per 1320, the capacitive sensing can be improved by adjusting a physical parameter of the electrodes and/or the particle for capacitive sensing. As above, the two-dimensional structure or system as illustrated in any of the structures and systems of the present disclosure, including structure 200, system 300, structure 500A, etc. can be used to facilitate the techniques discussed below or otherwise in the present disclosure. For example, the electrical materials associated with the sensors can be adjusted in relation to the properties of the particle to be deposited through the structure, and/or, in one embodiment, if the identity of the particle is roughly know by iterative application of sensing techniques or otherwise known, including but not limited to those disclosed herein, then the materials used for the electrodes can be adjusted accordingly. The particle can also have its physical attributed altered by applying a chemical or physical process to the particle in a way that is known to influence its electrical properties, and based on a comparison of the baseline measurement in relation to the altered particle, which was affected by the substance in a known way in relation to electrical properties, e.g. dielectric constant, the identity of the particle can be determined. In one embodiment, a computer device, e.g. 300, can be used to carry out 1310, 1320 and can further adjust, per 1330, a display, e.g. 330, of a system to display the difference in physical properties on the display, e.g. a difference in dielectric constant which translates to a difference in capacitance, on the display (this can apply equally to the fluid carrying the particle, e.g. one image with a certain contrast for the fluid and a different one for the particle). The display can have a contrast or one image for the fluid and one contrast or image for the particle, where the image is based on a change in the dielectric sensing of the sensing capacitive pairs, e.g. the computer 330 can cause a different display as different capacitive measurements are provided thereto. Per 1340, the capacitance is determined based on the comparison of the measured difference of the physical parameters, e.g. dielectric constant, associated with the physical change of the altered particle in relation to the baseline particle. In 1350, the type of particle, e.g. bacteria, chemical, or virus type can be determined based on the measured difference and/or the size of the particle can be determined based on the difference.

FIG. 14 illustrates a method 1400 for detecting a particle transmitted through a two-dimensional sensing structure according to an embodiment of the present disclosure. As above, the two-dimensional structure or system as illustrated in any of the structures and systems of the present disclosure, including structure 200, system 300, structure 500A, etc. Per 1410, a bio-particle is deposited through a two-dimensional capacitive sensing structure, e.g. 200, where per 1420 the bio agent, e.g. a virus, bacterium, or antibody, is combined with a substance that can affect it, e.g. a medication, vaccine, or other material or chemical known to affect the particular bio-agent in question. Per 1430, the system, e.g. 300, determines whether the substance changed based on a detected change in capacitance, and if it has, per 1440 the bio-agent type, e.g. virus or specific virus (Ebola), is determined based on the capacitive differences caused by the substance on the bio-agent, where, as above, a base line capacitance for the specific bio agent can be obtained by iterative experimentation with measurements for a particular bio agent and transmission fluid associated therewith, in relation to an unknown bio agent in a fluid deposited though a two-dimensional sensing structure.

Figure 15C:
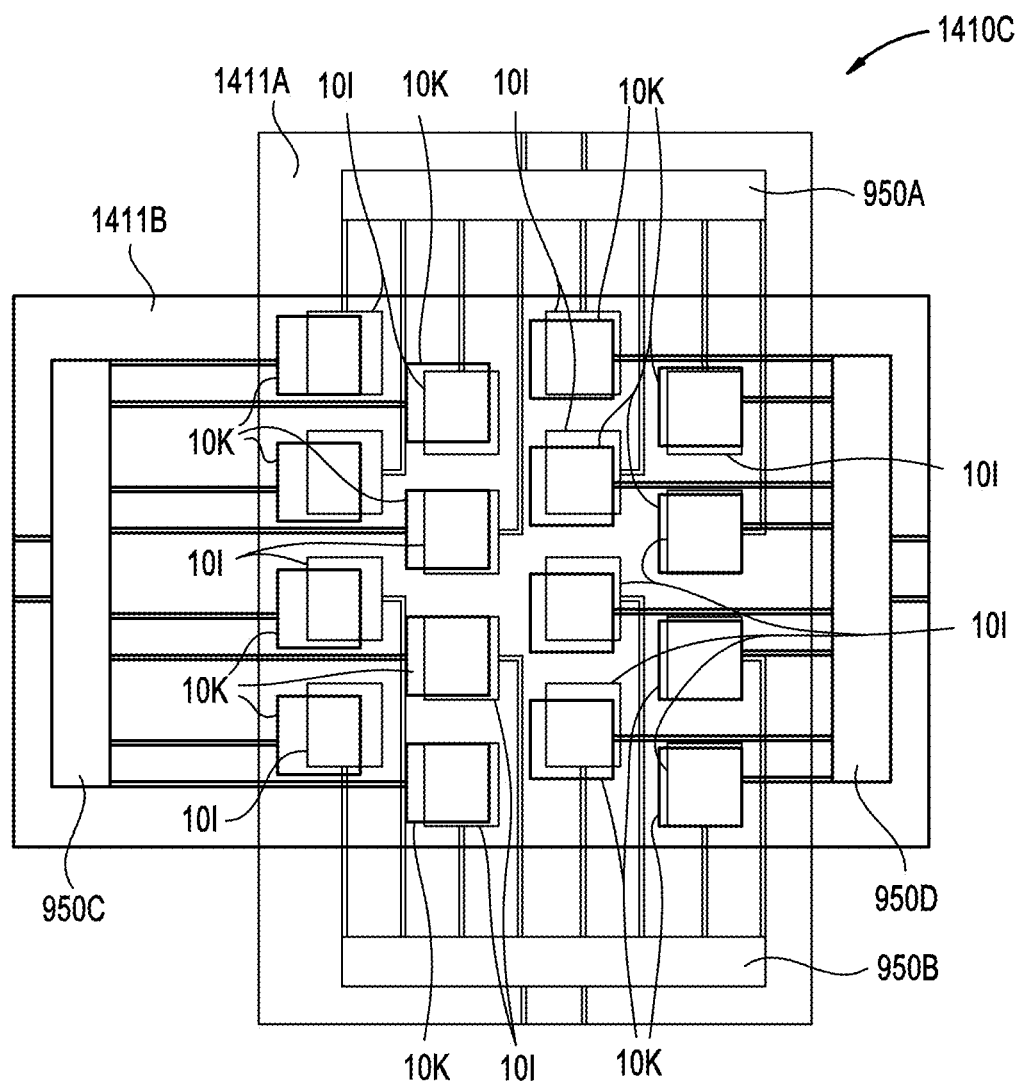
FIG. 15C illustrates a structure that is useful for two-dimensional (2-D) capacitive sensing, where the structure includes at least one integrated circuit useful for dimensional (2-D) capacitive sensing, in accordance with at least one embodiment of the present disclosure.

FIGS. 15A and 15B, illustrate structures that can form 2-D capacitive sensing structures in accordance with the teaching of the present disclosure, where 1400A includes substrate 50Q, electrodes 10L, and conductive lines 15L and 1400B includes electrodes 10K, substrate 50R, and conductive lines 15K. Per one embodiment, any differences in configuration are shown in the FIG. 15A and FIG. 15. Both structures have integrated circuits 930A, 930B, 930C, and 930D, where the integrated circuits 930A, 930B, 930C, and 930D connect to each individual conductive lines and electrode as shown. A staggered configuration of structures 1400A and 1400B is shown in FIG. 15C, but other configurations are possible as discussed above and as otherwise disclosed herein. In one embodiment, any one of the integrated circuits, e.g. 950A, 950B, etc. can receive a signal from one or more of the individual electrodes and conductive lines and/or can receive a signal from one or more of the conductive lines, which can mitigate noise from external sources that could otherwise influence the capacitive measurement and/or can provide a way of selecting individual electrodes and lines. In embodiment, conductors from electrodes 10I and 10K have the flexibility to exit to the edge of the substrate 50Q and 50R, respectively, in different directions (as shown) or in the same direction. The various configurations, material compositions, and selection methods discussed above or elsewhere herein, and with respect to any one of the components, systems, and configurations of the same, e.g., electrodes, 10K, 10L, conductive lines, 15K, 15l, etc. can, in one or more embodiments, apply to structures and systems that incorporate one or more embodiments that utilize integrated circuits (as discussed herein). In one embodiment, the integrated circuit is configured to detect i) a voltage change, ii) a capacitance change or iii) a current change at a point corresponding to movement by the at least one particle through the two-dimensional electrode structure.

Figure 16:
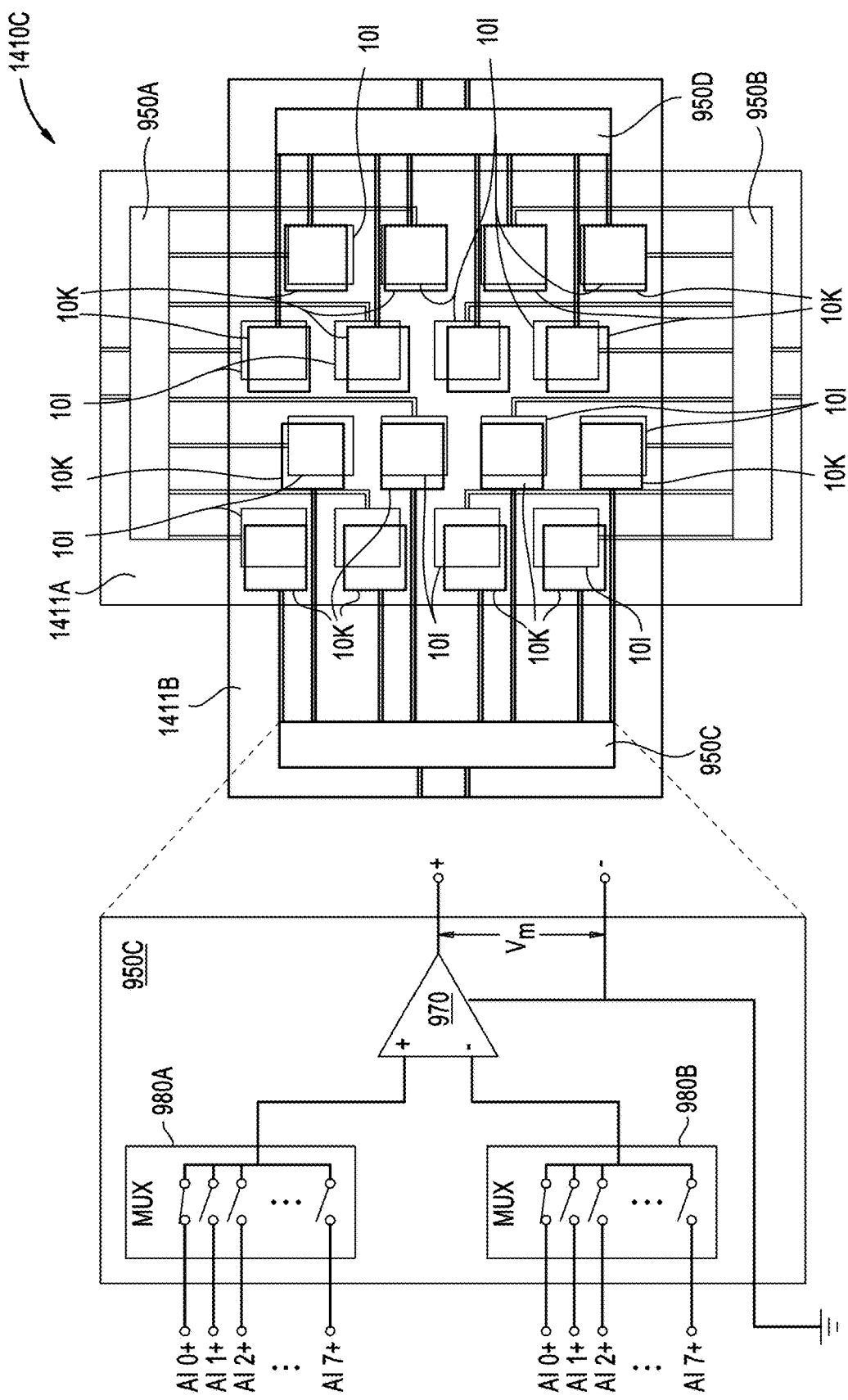
FIG. 16 illustrates a system that is useful for two-dimensional (2-D) capacitive sensing, where the structure includes at least one integrated circuit useful for dimensional (2-D) capacitive sensing, in accordance with at least one embodiment of the present disclosure.

FIG. 16 illustrates a structure 1410C, with a more detailed view of the constitution of an integrated circuit, e.g. 950C, as connected in the structure of FIG. 15C. In one embodiment, integrated circuit can include one or more multiplexers 980A, 980B, which can be used for selecting one or more lines and electrodes for sensing. The integrated circuit, e.g. 950C, can also include an amplifier 970 that can adjust the amplitude or other electrical properties associated with signals received by the integrated circuit 950C by one or more electrodes and conductive lines. In one embodiment, this is useful when dealing with extremely small particles, e.g. tens of nanometers in dimensions, and capacitive changes might correspond to signals with weak amplitude characteristics and/or signals that can be affected by external noise, as the multiplexer 980A, 980B, can isolate one line and associated electrode for sensing, and/or the amplifier 970 can enhance the signal, e.g. current or voltage amplitude, for a better read. The circuit 950C can be configured to cancel noise effect caused by defective electrodes and/or other electrodes as a result of the amplification and isolation features discussed herein. In one embodiment, the multiplexer, e.g. 950C, can rapidly select, e.g. in millisecond or nanosecond intervals, between the various electrodes to determine capacitive changes. In one embodiment, the amplifier 970, for example in integrated sense circuit 950C, can be a differential amplifier that amplifies the capacitance difference, for example, between one or more (depending on the multiplexer(s) 980A and 980B selector settings) electrode pairs. As is consistent with the above discussion, an electrode pair is one electrode 10I and one electrode 10K. Multiplexer(s) 980A and 980B are shown as having eight inputs each, A10 through A17 to match the eight conductors extending from the eight electrodes outwards towards the edge of each side of substrate 1411A and 1411B. In one embodiment, this can be accomplished with two integrated circuits, for example, shared between substrates 1411A and 1411B. As shown, the flexibility of incorporating four integrated circuits, 950A, 950B, 950C and 950D is provided. It is understood that the multiplexer 980A and 980B can have more or fewer than eight inputs, for example, to accommodate a different number of conductors connecting the electrodes, e.g. 10I and 10K. Since in some embodiments, e.g. bio-agent embodiment, a particle will flow throughout the structure, this enhances the probability that the system 1410 C can obtain an isolated signal corresponding to a point in time where a relevant particle is located in a prime location between the one or more electrode pairs. In one embodiment, the amplifier can amplify the isolated signal to improve the read. In one embodiment, as shown, one or more integrated circuits, e.g. 950A and 950C can be embedded on different substrates, 50Q, 50R or as with 950A and 950C, the same substrate, 50Q.

Figure 17:
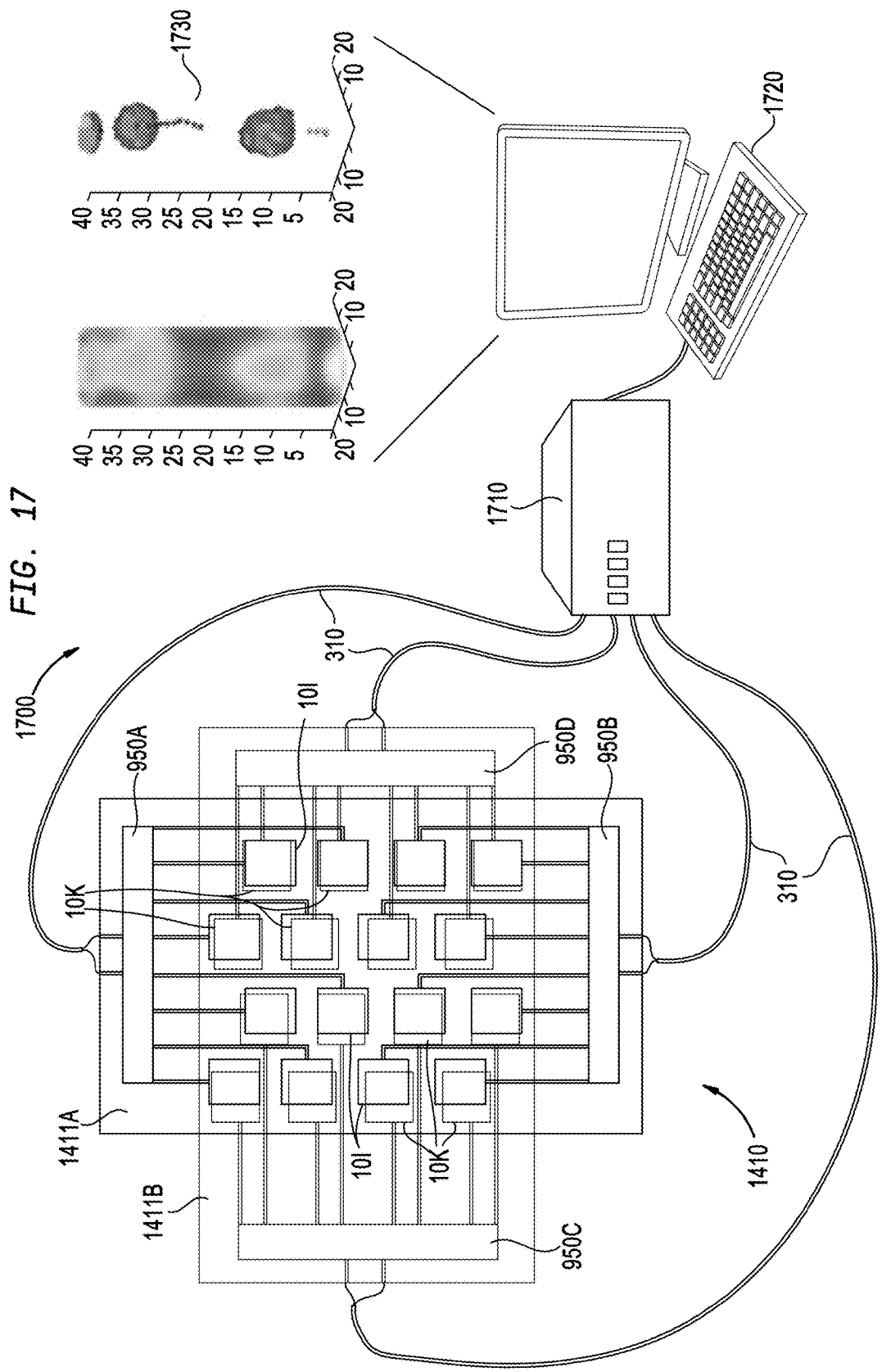
FIG. 17 illustrates a system that is useful for two-dimensional (2-D) capacitive sensing, where the structure includes at least one integrated circuit useful for dimensional (2-D) capacitive sensing, in accordance with at least one embodiment of the present disclosure.

FIG. 17 illustrates a system 1700 for capacitive sensing, that includes a data acquisition system or data acquisition device 1710 connected to one or more integrated circuits, e.g. 950C, of structure 1410C, and a computer with display device 1720. According to one embodiment, since the integrated circuit can select one electrode pair or electrode measurement at a time, the data acquisition system can acquire data related to the performance associated therewith. As it receives data, it can make a determination as to operability and effectiveness, and relay that information to the computer device 1720, which in turn can instruct system 1710 to disable or enable an electrode or electrode pair, or obtain more or less measurements, at an adjusted frequency, of one or more electrodes. In one embodiment, the computer 1720, based on data acquired from the data acquisition system 1710, can detect a particular pattern of repeated movement throughout the system, e.g. by taking multiple readings, and the pattern of movement can be correlated to particular particle, such as a bio-agent. According to this embodiment, the determination as to motion and identification of the particle can occur at any electrode pair and/or it can be based on a pattern of repeated movements obtained from one or more isolated electrode pairs. In one embodiment, the one or more integrated circuits can alter at least one of i) voltage, ii) current, iii) frequency, or iv) shape of a waveform associated with the received input signal from the one or more electrode pairs, and to provide the altered signal as an output to the data acquisition device 1710. In one embodiment, in lieu of or in conjunction with system 1710, the integrated circuit can include one or neural networks to determine the pattern of repeated movement based on an iterative process that accounts for the pattern of movement of the plurality of particles, and adjust a timing sequence by which the multiplexer selects the one or more electrode pairs based on the iterative process. For convenience, in one embodiment, the neural network is represented by the amplifier symbol 970, even though a neural network can include one or more functionalities that extend beyond amplification.

The integrated circuit, e.g. 950C, can supply a consolidated signal from one or more electrode pairs to the data acquisition system 1710, which in turn can supply the consolidated signal to the computer device. In certain embodiments, a consolidated signal, in accordance with the teachings contained herein, may provide sufficient information to identify a particle.

Figure 18A:
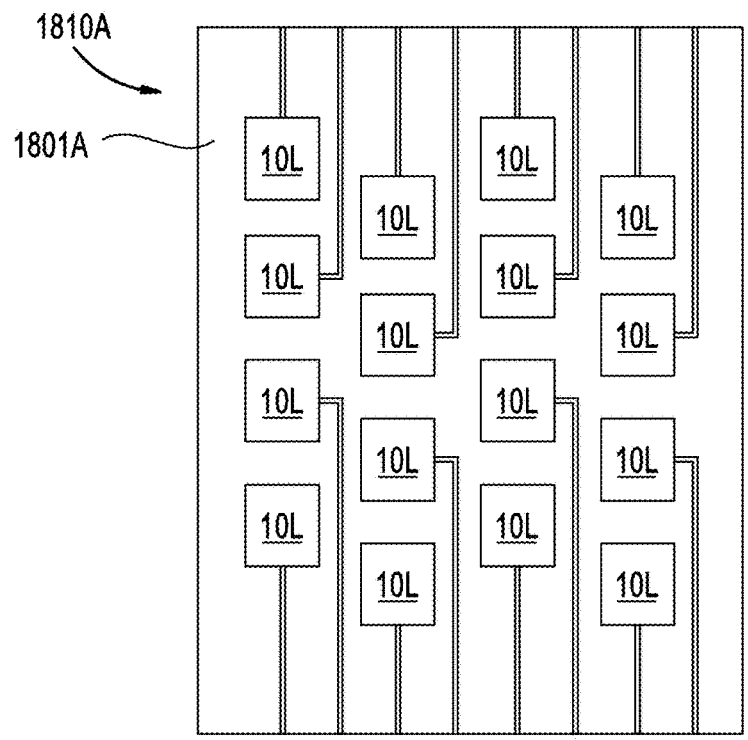
FIG. 18A illustrates a structure that is useful for two-dimensional (2-D) capacitive sensing, where the structure includes at least one via connection useful for dimensional (2-D) capacitive sensing, in accordance with at least one embodiment of the present disclosure.
Figure 18B:
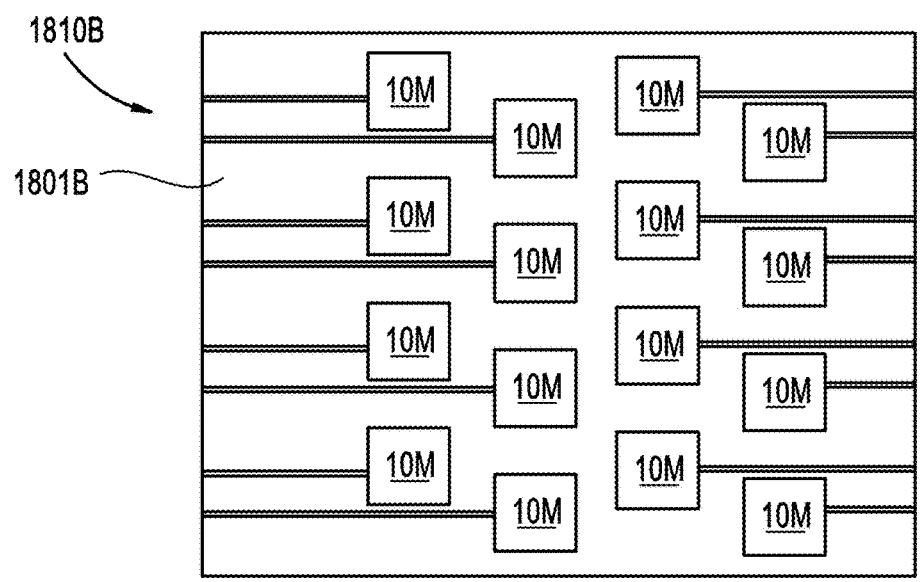
FIG. 18B illustrates a structure that is useful for two-dimensional (2-D) capacitive sensing, where the structure includes at least one via connection useful for dimensional (2-D) capacitive sensing, in accordance with at least one embodiment of the present disclosure.
Figure 18C:
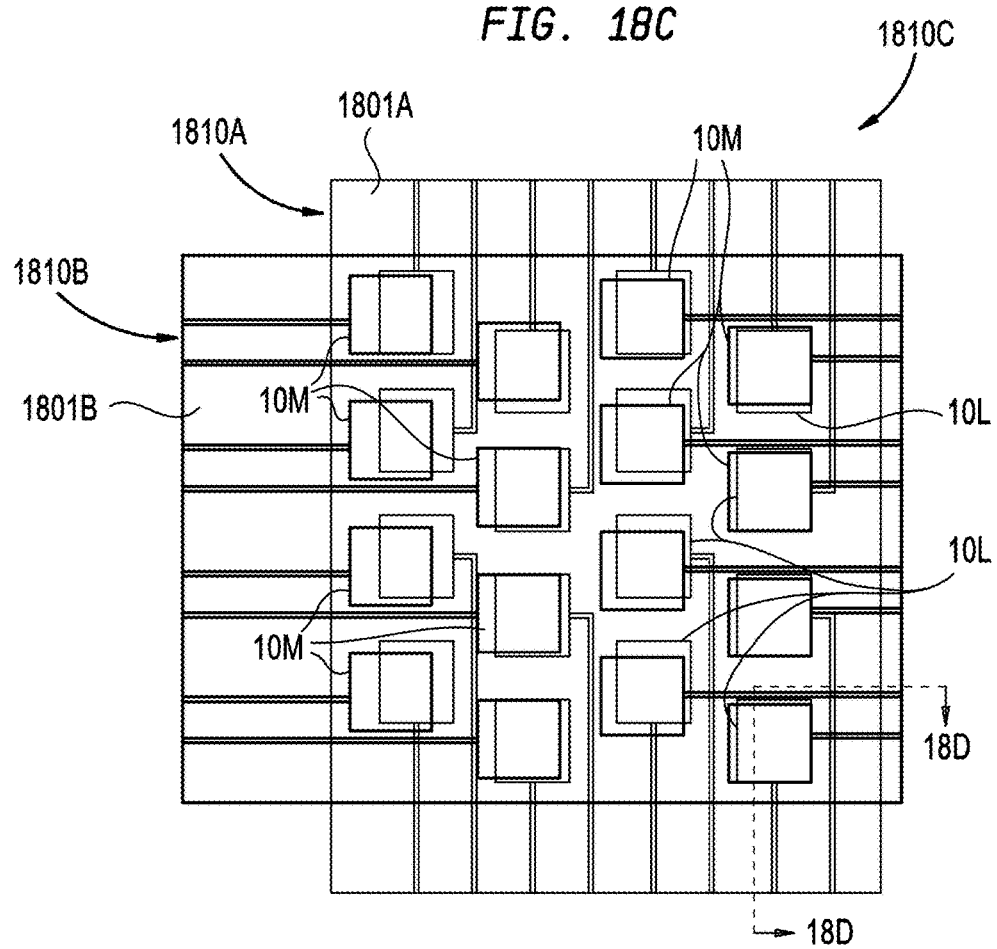
FIG. 18C illustrates a two-dimensional (2-D) sensing structure that is useful for two-dimensional (2-D) capacitive sensing, where the structure includes at least one via connection useful for dimensional (2-D) capacitive sensing, in accordance with at least one embodiment of the present disclosure.
Figure 18D:
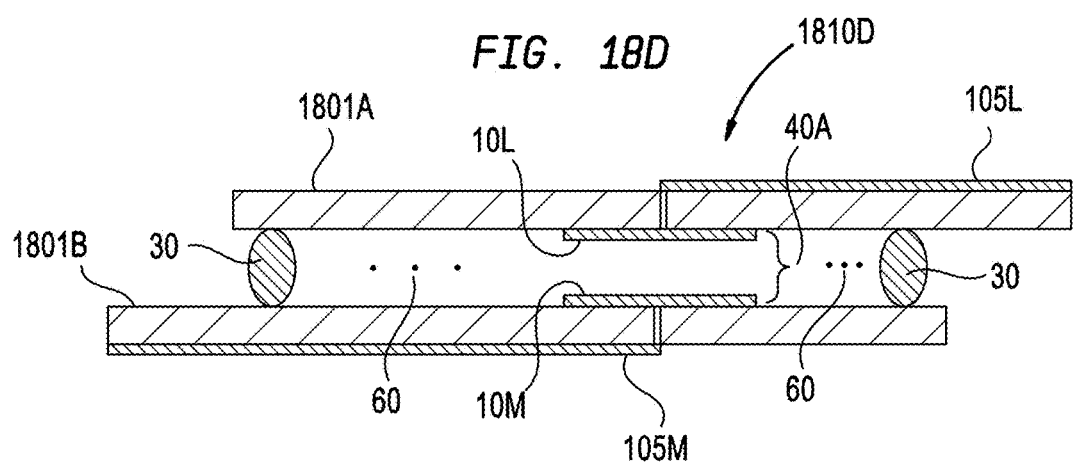
FIG. 18D illustrates a sensing cross-section of a two-dimensional (2-D) sensing structure that is useful for two-dimensional (2-D) capacitive sensing, where the structure includes at least one via connection useful for dimensional (2-D) capacitive sensing, in accordance with at least one embodiment of the present disclosure.

FIG. 18A, FIG. 18B, and FIG. 18C show sensing structures in accordance with one or more configurations as disclosed in the present disclosure, where the electrodes, conductive lines, etc. and other components therein can be configured as stated herein and include one or more materials for each, as disclosed herein. In one embodiment, as shown in the cross section shown in FIG. 18D, which is a cross section of structure 1810C, itself including structure 1810A overlaid with structure 1810B, each electrode, 10M, 10L, and by extension all pairs therefrom, have a direct connection to a thru via, 105 M, 105L. As above, structures 1810A, 1810B include substrates 1801A, 1801B, respectively. The one or more vias can be embedded in the one or more substrates, 50M, 50L. In one embodiment, electrodes 10L and 10M may exit to the edge of the substrate 1801A and 1801B, respectively, in different directions (as shown) or in the same direction. Further, electrodes 10L and 10M may each connect through one (shown) or more vias that allow additional flexibility of the electrodes 10L and 10M of exiting to the edge of the substrate 1801A and 1801B, respectively, from the top or the bottom of their respective substrates, The direct connection to a via, e.g. 105L, dramatically reduces cross-talk between electrodes, and it also provides a cleaner, essentially noise-free signal, e.g. reduces parasitic capacitance associated with cross-talk and/or other noise. In one embodiment, the interference mitigation and noise cancellation can be configured when one or more of the substrates, 50M, 50L, are a ground plane.

In one embodiment, one or more of the substrates, 50M, 50L, as a result of the one or more via connection, form a faraday cage that prohibits parasitic interference among one or more conductive lines on the same substrate and/or on a different substrate.

In one embodiment, each one of the first substrate 50L and the second substrate 50M includes a metal, and where an interface oxide layer or other insulation layers (not shown) coats each substrate at a respective interface where each one the one or more first vias exists the first substrate 50L and where each one of the one or more second via exists the second substrate 50M. In this embodiment, the oxide or insulation layer provides another advantage by isolating each electrode from neighboring electrodes, thus enabling cleaner signal detection by further mitigating parasitic capacitance.

Figure 18E:
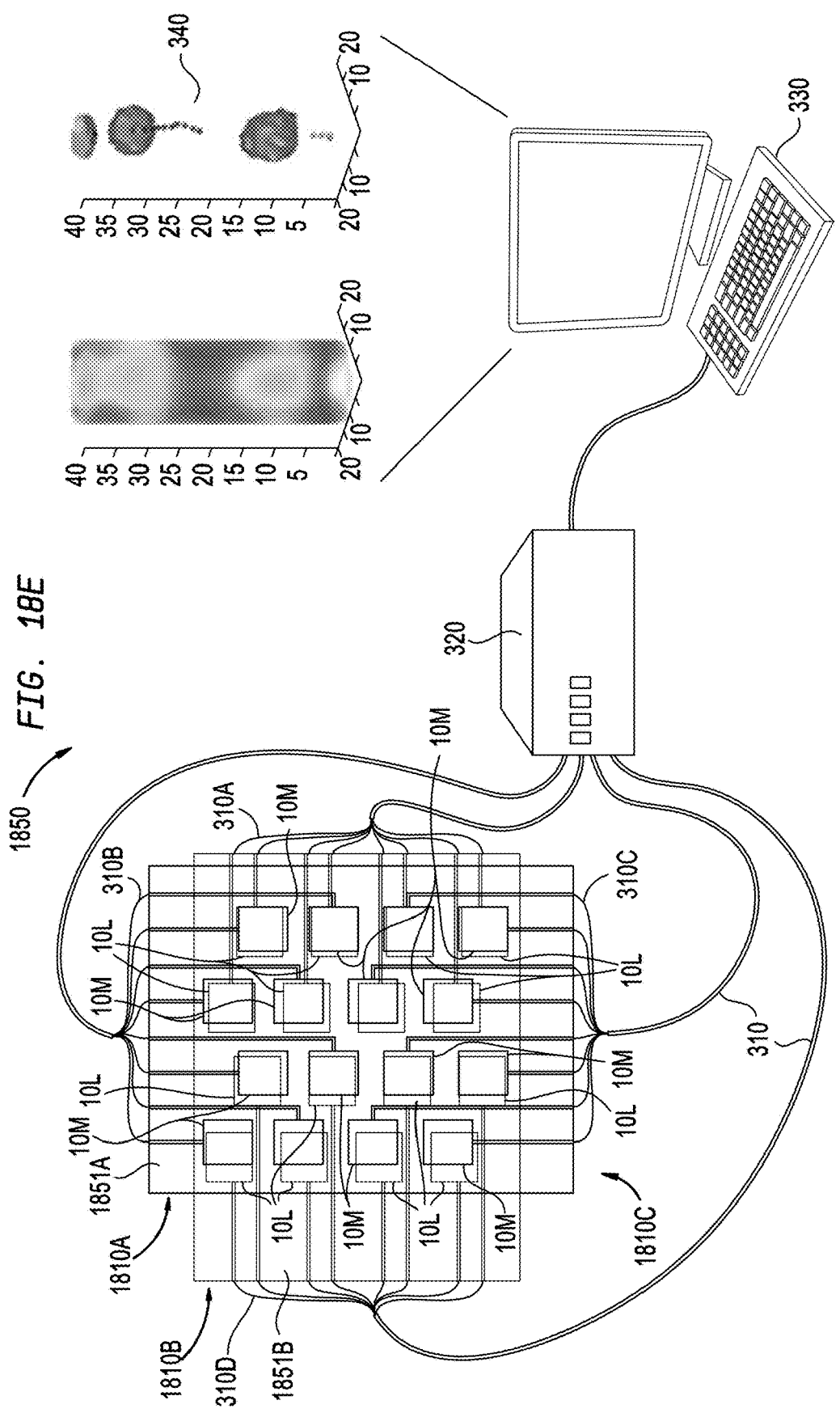
FIG. 18E illustrates a two-dimensional (2-D) sensing system that is useful for two-dimensional (2-D) capacitive sensing, where the system includes at least one via connection useful for dimensional (2-D) capacitive sensing, in accordance with at least one embodiment of the present disclosure.

FIG. 18E illustrates applying the structure 1810C to a system as disclosed in the present disclosure, in order to provide better signals to the relevant components as disclosed therein, e.g. 320 and 330.

The one or more vias can include any conductive material, such as a metal, or dielectric material, or they can be composed of any other conductive or dielectric material as disclosed herein or otherwise known.

FIG. 18F and FIG. 18G show a structure 1830B, and a cross section 1830E thereof, that overlays 1801C and 1801D, e.g. structures substrates with electrodes (e.g., 10O, 10P) thereon, and shows a configuration where each electrode, 10O, 10P and each electrode pair has a conductive via, e.g. 10X, connected thereto, thus reducing parasitic interference throughout the entire structure 1830B.

FIG. 19 illustrates a method 1900 for detecting a particle transmitted through a two-dimensional sensing structure according to an embodiment of the present disclosure, where the method can employ one or more structures, systems, and other methods disclosed herein, including the structures and systems shown in FIG. 15A-FIG. 18G. Per 1900, a particle is deposited through a two-dimensional capacitive sensing structure, where an integrated circuit performs a select or receive operation on electrodes and electrode pairs that detect the particle, as disclosed above and herein or as is otherwise suitable pursuant to the teachings contained herein.

FIG. 20 illustrates a method 2000 for detecting a particle transmitted through a two-dimensional sensing structure according to an embodiment of the present disclosure, where the method can employ one or more structures, systems, and other methods disclosed herein, including the structures and systems shown in FIG. 15A-FIG. 18G. Per 2010, a particle is deposited through a two-dimensional capacitive sensing structure, where in 2020 the particle is suspended in a liquid medium or fluid that has physical parameters suitable for traversing the two-dimensional structure. Per 2030, an integrated circuit performs a select or receive operation on electrodes and electrode pairs that detect the particle, as disclosed above and herein or as is otherwise suitable pursuant to the teachings contained herein, and based on data acquired from the select/receive operations, e.g. provided to a data acquisition system, a computer can instruct the integrated circuit (via the data acquisition system or otherwise) to disable one or more defective or extraneous electrodes.

Figure 21:
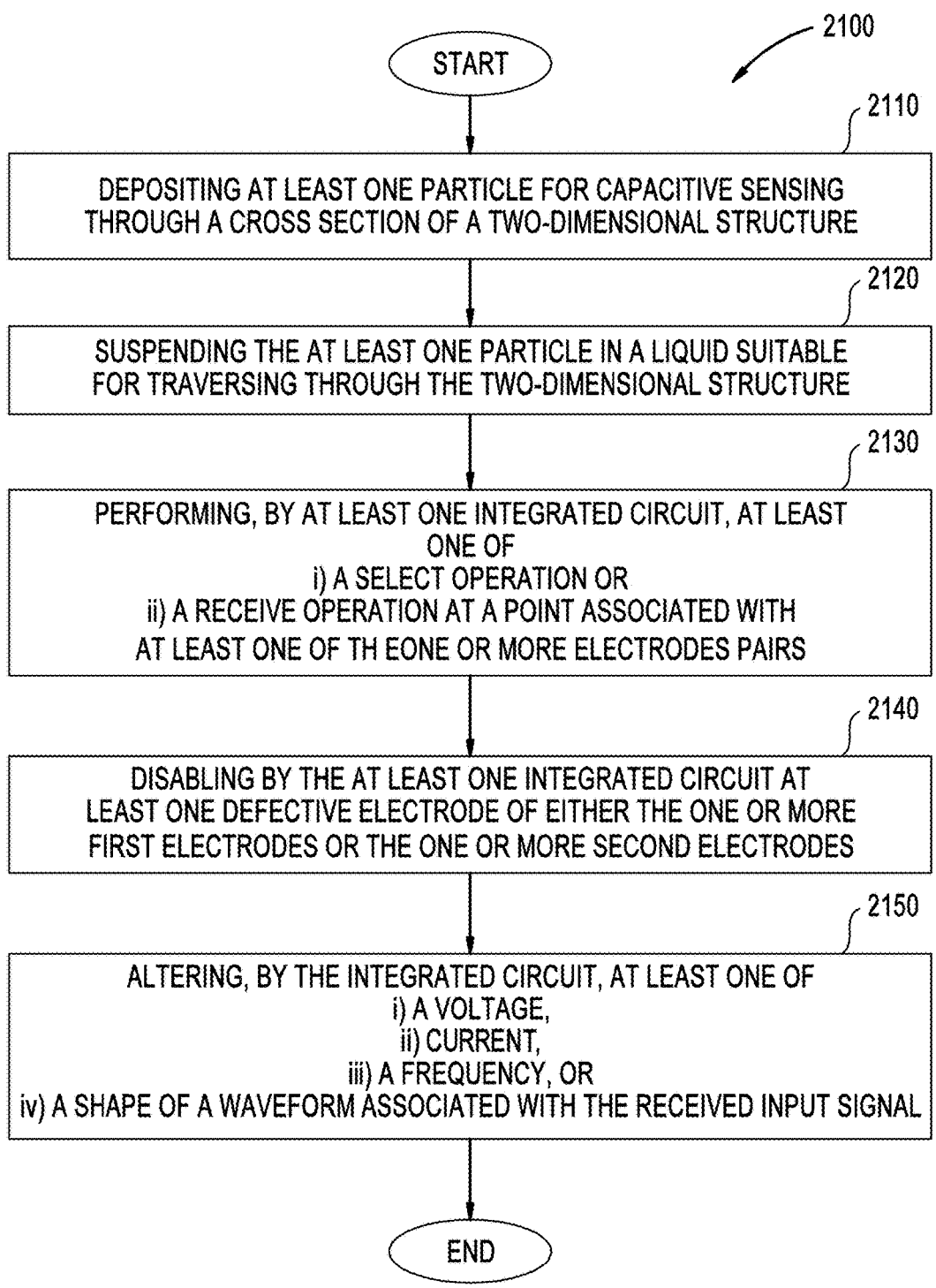
FIG. 21 illustrates a method for two-dimensional (2-D) capacitive sensing in accordance with at least one embodiment of the present disclosure.

FIG. 21 illustrates a method 2000 for detecting a particle transmitted through a two-dimensional sensing structure according to an embodiment of the present disclosure, where the method can employ one or more structures, systems, and other methods disclosed herein, including the structures and systems shown in FIG. 15A-FIG. 18G. Per 2110, a particle is deposited through a two-dimensional capacitive sensing structure, where in 2120 the particle is suspended in a liquid medium or fluid that has physical parameters suitable for traversing the two-dimensional structure. Per 2130, an integrated circuit performs a select or receive operation on electrodes and electrode pairs that detect the particle, as disclosed above and herein or as is otherwise suitable pursuant to the teachings contained herein, and based on data acquired from the select/receive operations, e.g. provided to a data acquisition system, a computer can instruct the integrated circuit (via the data acquisition system or otherwise) to disable one or more defective or extraneous electrodes. Per 2150, the integrated circuit can adjust an electrical parameter of incoming signals to compensate or adjust for the disabled electrodes.

Although the above examples, techniques, and embodiments are directed towards two-dimensional capacitive sensing, at least one embodiment can be adjusted for resistive sensing. For example, the electrodes and structures of FIG. 2A-FIG. 3 could be resistive elements, e.g. composed of suitable resistive materials, as oppose to capacitive materials. For many materials or samples, the current (I) through the material or sample is proportional to the voltage across it. The electrical resistance, R, of an object is defined as the ratio of voltage across it, V, to current through it, I, while conductance, G, is defined as the inverse:

$$R = V/I, \quad G = I/V = 1/R \tag{Equation 5}$$

Other materials or samples do not obey the above current-to-voltage constant R proportionality, but the resistance varies with the voltage and current through it in a nonlinear fashion. In these nonlinear resistance samples, the differential resistance, $$R_{\textit{diff}} = V/dI, \tag{Equation 6}$$

This is defined as the first derivative of the voltage with respect to the current, is more useful. In general, the resistance and conductance is mostly determined by two properties; (1) the geometry, such as the cross sectional area, A, and the length, l, and (2), the material itself, such as the material resistivity, $\rho$, or it's inverse relationship, conductivity, $\sigma$, defined as:

$$R = \rho(l/A), \quad G = \sigma(A/l) \tag{Equation 7}$$

Therefore, resistive, or conductive sensing is useful for identifying the material and/or geometry of the material. An ideal electrical resistive or conductive sensing circuit has a large measurement range, has a high resolution, and most importantly, has no leakage paths/good noise immunity.

Direct Current (DC) or Alternating Current (AC), such as ramped, sinusoidal, or pulsed based conductance measurement techniques is possible.

In the AC techniques applied to materials, not only is the current-to-voltage ratio magnitudes possible, but also the current-to-voltage phase differences and possibly other data such as frequency dependence, material strain dependence, light illumination dependence and temperature dependence. These techniques may employ balanced bridge circuits and/or high-performance operational amplifiers and require passive components such as resistors and, and in some cases, capacitors. A simple measurement circuit implementation may involve two terminal inputs/outputs (I/Os) contacting the sample under measurement, where a voltage is applied across the two terminals, and a corresponding current flow is measure into/out of these two terminals, where the structure configurations of the resistors and devices would conform to at least one configuration as disclosed herein. Another implementation may involve four terminals contacting the sample under measurement along the same conductance/current flow path, where the outer most two terminals are dedicated to inducing a current, and the inner two terminals are dedicated to high accuracy/low noise voltage measurements.

A difficulty that can arise and is associated with a four-terminal implementation is the scaling down of the I/O terminals so that the voltage terminals create minimum measurement interference, both physically and electrically, in contacting the actual sample under measurement. For example, the width of the somewhat conductive voltage measurement terminal will electrically short out the sample region it is in contact with across the width of the terminal and altering the electrical field, so minimization of this terminal point contact with the sample minimizes these measurement artifacts.

The configurations shown herein with respect to the capacitors can provide optimized groups of two and/or four electrode terminals.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. A structure for sensing material movement, comprising:
   one or more first conductive lines arranged in a first arrangement in relation to a first substrate,
   one or more second conductive lines connected arranged in a second arrangement in relation to a second substrate;
   one or more first vias embedded on the first substrate and connecting one or more first electrodes to each respective one of the one or more first conductive lines; and
   one or more second vias embedded on the second substrate and connecting the one or more second electrodes to each respective one of the one or more second conductive lines,
   wherein the one or more first conductive electrodes and the second one or more electrodes are parallel and overlapping with respect to one another, and
   wherein i) the one or more first conductive electrodes and ii) the one or more second conductive electrodes form a two-dimensional sensing configuration.

2. The structure according to claim 1, wherein the one or more first vias are in a distinct plane in relation to both the one or more first electrodes and the one or more first conducting lines, and wherein each one of the first one or more electrodes and each corresponding one of the second one or more electrodes forms one or more electrode pairs configured to receive at least one particle for capacitive sensing.

3. The structure according to claim 2, wherein the one or more second vias are in a distinct plane in relation to both the one or more second electrodes and the one or more second conductive lines.

4. The structure according to claim 3, wherein the each one of the first substrate and the second substrate comprises an opaque material.

5. The structure according to claim 3, wherein each one of the first substrate and the second substrate comprises a transparent material.

6. The structure according to claim 4, wherein each one of the first substrate and the second substrate comprises a metal, and wherein an interface oxide layer coats each substrate at a respective interface where each one of the one or more first vias exits the first substrate and where each one of the one or more second via exits the second substrate.

7. The structure according to claim 3, wherein the first substrate is a ground plane that electrically isolates each one of the one or more second conductive lines from communicating with another one of the one or more second conductive lines.

8. The structure according to claim 7, wherein the second substrate is a ground plane that electrically isolates each one of the one or more first conductive lines from communicating with another one of the one or more first conductive lines.

9. The structure according to claim 8, wherein each one of the first substrate and the second substrate form a faraday cage that prohibits parasitic interference among i) each of the one or more first conductive lines and another one of the one or more first conductive lines, ii) each one of the one or more second conductive lines and another one of the one or more second conductive lines, and iii) each one of the one or more first conductive lines and each one of the one or more second conductive lines.

10. The structure according to claim 9, wherein each one of the first substrate and the second substrate form a faraday cage that prohibits parasitic interference among i) each of the one or more first conductive electrodes and another one of the one or more first conductive electrodes, ii) each one of the one or more second conductive electrodes and another one of the one or more second conductive electrodes, and iii) each one of the one or more first conductive electrodes and each one of the one or more second conductive electrodes.

11. A method comprising:
depositing at least one particle for capacitive sensing through a cross section of a two-dimensional structure, wherein the two-dimensional structure comprises: i) a first plane associated with a first substrate containing one or more first conductive electrodes and ii) a second plane associated with a second substrate containing one or more second conductive electrodes, wherein the one or more first conductive electrodes and the one or more second electrodes are overlapping with respect to one another, and wherein the i) one or more first conductive electrodes and ii) the one or more second conductive electrodes form a two-dimensional sensing configuration;
connecting, respectively, the one or first conductive electrodes to one or more first conductive lines by one or more first vias; and
connecting, respectively, the one or second conductive electrodes to one or more second conductive lines by one or more second vias, wherein each one of the one or more first electrodes and each corresponding one of the one or more second electrodes forms one or more electrode pairs configured to receive at least one particle for sensing.

12. The method according to claim 11 comprising: reducing parasitic interference by placing the one or more first vias on a distinct plane from both the one or more first conductive lines and the one or more first electrodes.

13. The method according to claim 12 comprising: reducing parasitic interference by placing the one or more second vias on a distinct plane from both the one or more second conductive lines and the one or more second electrodes.

14. The method according to claim 13, wherein the reduced parasitic interference associated with both substrates enables a linear n/2 number of sensing measurements with respect to the at least one particle, where n refers to a total number of electrodes associated with the two-dimensional sensing structure.

15. The method according to claim 14, wherein the first substrate is a ground plane that electrically insulates each one of the one or more first conductive lines from communicating with another one of the one or more first conductive lines.

16. The method according to claim 15, wherein second substrate is a ground plane that electrically insulates each one of the one or more second conductive lines from communicating with another one of the one or more first conductive lines.

17. The method according to claim 16, wherein each one of the first substrate and the second substrate form a faraday cage that prohibits parasitic interference among i) each of the one or more first conductive lines and another one of the one or more first conductive lines, ii) each one of the one or more second conductive lines and another one of the one or more second conductive lines, and iii) each one of the one or more first conductive lines and each one of the one or more second conductive lines.

18. The method according to claim 17, wherein each one of the first substrate and the second substrate form a faraday cage that prohibits parasitic interference among I) each of the one or more first conductive electrodes and another one of the one or more first conductive electrodes, ii) each one of the one or more second conductive electrodes and another one of the one or more second conductive electrodes, and iii) each one of the one or more first conductive electrodes and each one of the one or more second conductive electrodes.

19. A system comprising:
a two-dimensional electrode structure comprising:
one or more first conductive electrodes in a first plane associated with a first substrate,
one or more second conductive electrodes in a second plane associated with a second substrate,
one or more dielectric materials between the first plane and the second plane,
one or more first conductive lines connected, in a first arrangement in relation to the first substrate, to the first one or more conductive electrodes,
one or more second conductive lines connected, in a second arrangement in relation to the second substrate, to the second one or more conductive electrodes,
one or more first vias connecting the one or more first electrodes to each respective one of the one or more first conductive lines, and
one or more second vias connecting the one or more second electrodes to each respective one of the one or more second conductive lines,
wherein the one or more first conductive electrodes and the one or more second electrodes are overlapping with respect to one another, wherein i) the one or more first conductive electrodes and ii) the one or more second conductive electrodes form a two-dimensional sensing configuration, wherein the one or more first conductive electrodes and the one or more second conductive electrodes are overlapping with respect to one another, wherein the i) one or more first conductive electrodes and ii) the one or more second conductive electrodes form a two-dimensional sensing configuration, and
a multi-sensing computer device connected to the two-dimensional electrode structure via i) the one or more first conductive lines and ii) the one or more second conductive lines configured to:
enable and/or disable at least one of the i) at least one of the one or more first conductive electrodes and ii) at least one of the one or more second conductive electrodes to form an electrode configuration that corresponds to a physical characteristic of the at least one particle,
sense a change in capacitance corresponding to the at least one particle traveling through the two-dimensional structure with the electrode configuration that corresponds to a physical characteristic of the at least one particle, and
a display connected to the multi-sensing computer device, wherein the display displays the at least one particle based on the sensed change in capacitance.

20. The system according to claim 19, wherein the first substrate is a ground plane that electrically insulates each one of the one or more first conductive lines from communicating with another one of the one or more first conductive lines, and wherein second substrate is a ground plane that electrically insulates each one of the one or more second conductive lines from communicating with another one of the one or more first conductive lines.

* * * * *